US009402560B2

(12) United States Patent
Organ et al.

(10) Patent No.: US 9,402,560 B2
(45) Date of Patent: Aug. 2, 2016

(54) ADVANCED MULTI-PURPOSE CATHETER PROBES FOR DIAGNOSTIC AND THERAPEUTIC PROCEDURES

(75) Inventors: Leslie W. Organ, Charleston, SC (US); George Peter Darmos, Toronto (CA); Ilya Gavrilov, Mississauga (CA); Peter George Darmos, Toronto (CA)

(73) Assignee: Diros Technology Inc., Markham (CA)

( * ) Notice: Subject to any disclaimer, the term of this patent is extended or adjusted under 35 U.S.C. 154(b) by 1033 days.

(21) Appl. No.: 13/188,101

(22) Filed: Jul. 21, 2011

(65) Prior Publication Data

US 2012/0089123 A1   Apr. 12, 2012

Related U.S. Application Data

(60) Provisional application No. 61/399,912, filed on Jul. 21, 2010, provisional application No. 61/465,780, filed on Mar. 25, 2011.

(51) Int. Cl.
| | | |
|---|---|---|
| *A61B 18/18* | (2006.01) | |
| *A61B 5/053* | (2006.01) | |
| *A61B 5/01* | (2006.01) | |
| *A61B 18/14* | (2006.01) | |
| *A61B 18/00* | (2006.01) | |

(Continued)

(52) U.S. Cl.
CPC ............... *A61B 5/0538* (2013.01); *A61B 5/01* (2013.01); *A61B 18/1492* (2013.01); *A61B 2018/00577* (2013.01); *A61B 2018/00797* (2013.01); *A61B 2018/00875* (2013.01); *A61B 2018/1437* (2013.01); *A61B 2018/1497* (2013.01); *A61B 2218/002* (2013.01); *A61M 2025/0057* (2013.01); *A61N 1/36071* (2013.01); *A61N 1/36171* (2013.01)

(58) Field of Classification Search
CPC .... A61B 5/01; A61B 5/0538; A61B 18/1492; A61B 2018/00577; A61B 2018/00797; A61B 1/36171; A61B 2018/1437; A61B 2018/1497; A61B 2018/00875; A61B 2218/002
USPC ..................................................... 606/32–48
See application file for complete search history.

(56) References Cited

U.S. PATENT DOCUMENTS

| | | | | |
|---|---|---|---|---|
| 4,488,824 A | * | 12/1984 | Salem ...................... | G01K 7/13 374/178 |
| 4,532,924 A | | 8/1985 | Auth et al. | |
| 5,005,986 A | * | 4/1991 | Najjar ...................... | G01K 1/10 136/230 |

(Continued)

FOREIGN PATENT DOCUMENTS

| | | |
|---|---|---|
| CA | 2048449 | 2/1993 |
| WO | 2004078052 | 9/2004 |

*Primary Examiner* — Michael Peffley
*Assistant Examiner* — Amanda Zink
(74) *Attorney, Agent, or Firm* — Bereskin & Parr LLP S.E.N.C.R.L., s.r.l.

(57) ABSTRACT

Various embodiments are described herein that generally relate to catheter probes for diagnostic and/or therapeutic purposes. The catheter probes described herein generally comprise a proximal hub comprising a hub housing and at least one wire, a catheter body connected to the proximal hub, the catheter body comprising a channel member and an insulator, the channel member being adapted to provide a housing for a portion of the catheter body and a conductive pathway, and the insulator being adapted to cover at least a portion of the channel member; and a catheter distal end comprising at least one electrode connected to the at least one wire.

29 Claims, 9 Drawing Sheets

(51) Int. Cl.
*A61M 25/00* (2006.01)
*A61N 1/36* (2006.01)

(56) References Cited

U.S. PATENT DOCUMENTS

| | | | |
|---|---|---|---|
| 5,370,675 A * | 12/1994 | Edwards et al. | 607/101 |
| 5,435,308 A | 7/1995 | Gallup et al. | |
| 5,486,161 A * | 1/1996 | Lax et al. | 604/22 |
| 5,895,355 A * | 4/1999 | Schaer | 600/381 |
| 5,899,891 A | 5/1999 | Racz | |
| 5,957,961 A * | 9/1999 | Maguire et al. | 607/99 |
| 6,078,830 A * | 6/2000 | Levin et al. | 600/374 |
| 6,456,863 B1 | 9/2002 | Levin et al. | |
| 6,632,221 B1 | 10/2003 | Edwards et al. | |
| 7,318,822 B2 | 1/2008 | Darmos et al. | |
| 7,794,458 B2 | 9/2010 | McIntyre et al. | |
| 2002/0058866 A1 | 5/2002 | Segner et al. | |
| 2005/0137667 A1 | 6/2005 | Omar-Pasha et al. | |
| 2005/0273094 A1 * | 12/2005 | Ryan | 606/41 |
| 2005/0288663 A1 | 12/2005 | Behzadian | |
| 2007/0088244 A1 | 4/2007 | Miller et al. | |
| 2007/0149966 A1 * | 6/2007 | Dahla et al. | 606/41 |
| 2009/0306604 A1 | 12/2009 | Darmos et al. | |
| 2011/0160723 A1 * | 6/2011 | Tullis et al. | 606/41 |

* cited by examiner

ADVANCED MULTI-PURPOSE CATHETER PROBES FOR DIAGNOSTIC AND THERAPEUTIC PROCEDURES

CROSS-REFERENCE

This application claims the benefit of U.S. Provisional Application No. 61/399,912, filed Jul. 21, 2010, and also claims the benefit of U.S. Provisional Application No. 61/465,780, filed Mar. 25, 2011, and the entire contents of both are hereby incorporated by reference.

FIELD

Various embodiments are described herein that generally relate to multi-purpose catheter probes for diagnostic and/or therapeutic purposes.

INTRODUCTION

The insertion of catheters and probes into one of an epidural space, a spinal space, or a paravertebral space of a patient to treat chronic neurogenic pain not relieved by more conservative medical procedures is well known. For example, epidural catheters can be inserted into the epidural space and, by fluoroscopic and/or endoscopic guidance, reach a target area at which point local anesthetics and steroids can be injected to relieve the pain. The catheter can remain in place for one to 30 days, for example, and the injection of the medications can be made through external or implanted pumps.

Alternatively or in addition to the above treatment, a probe, inserted in combination with or sequential to the catheter, can be used to apply continuous or pulsed radiofrequency (RF) energy as a therapeutic modality to at least one of a nerve, a nerve root, a nerve ganglion, or a part of the spinal cord. Also, low frequency electrical stimulation can be used to assist with the identification of target structures prior to treatment with steroids or RF energy. Low frequency electrical stimulation can be used as well to assess the effectiveness of treatment by comparing sensory responses, for example in the lower limbs, before and after treatment.

Thus, the use of catheters and probes in epidural, spinal, and paravertebral spaces to treat chronic neurogenic pain is generally accepted, but is limited because conventional catheters and probes lack flexibility, or are too large to access some desired regions for treatment, or lack the range of functions required to effectively and safely provide treatment (i.e. conventional catheters and probes typically only provide one or two functions at most).

SUMMARY OF VARIOUS EMBODIMENTS

In one aspect, in at least one example embodiment described herein, there is provided a catheter probe comprising a proximal hub comprising a hub housing and at least one wire; a catheter body connected to the proximal hub, a catheter body connected to the proximal hub, the catheter body comprising a channel member and an insulator, the channel member being adapted to provide a housing for a portion of the catheter body and a conductive pathway, and the insulator being adapted to cover at least a portion of the channel member; and a catheter distal end comprising at least one electrode connected to the at least one wire.

In at least some embodiments, the channel member is adapted to provide the housing for a substantial portion of the catheter body.

In at least some embodiments, the channel member comprises one of a coil and a tube.

In at least some embodiments, the at least one electrode comprises a coil that is loosely wound to allow a fluid to be ejected from the catheter probe in use.

In at least some embodiments, the channel member extends into the catheter distal end and the at least one electrode comprises an uninsulated portion of the channel member in the catheter distal end.

In at least some embodiments, the channel member comprises a lumen and the catheter probe further comprises a tube located within the lumen of the channel member, the tube extending from the hub to the catheter distal end.

In at least some embodiments, the catheter distal end comprises an end portion spaced apart from an end portion of the tube, a first wire is connected to a portion of the tube within the hub and a second wire is connected near the at least one electrode to form a thermocouple junction for a thermocouple probe.

In at least some embodiments, the catheter probe further comprises a fluid injection port to receive a fluid in use; and a plastic tubing that extends from the fluid injection port into the hub, the plastic tubing having a first opening for receiving the fluid from the fluid injection port and a second opening extending between an inner wall of the channel member and an outer surface of the tube, wherein, in use, the fluid is provided from the plastic tubing through the second opening to the catheter body.

In at least some embodiments, the catheter probe further comprises a cylindrical insulator having a proximal portion and a distal elongated portion having a smaller outer diameter than the proximal portion; a first coil electrode that is on the elongated portion of the cylindrical insulator; an end portion formed by a distal end of the tube; and a distal portion of the channel member is uninsulated to provide a second coil electrode, wherein the cylindrical insulator is on the tube and is located adjacent the second coil electrode and the first coil electrode is located between the proximal portion of the cylindrical insulator and the end portion of the tube.

In at least some embodiments, the catheter probe comprises two temperature sensors located within the tube at locations near the first and second electrodes respectively, the temperature sensors being connected to electrical leads located within the tube and connected within the hub.

In at least some embodiments, the catheter probe comprises an insulated collar; and a first member defining the catheter distal end, the first member comprising an uninsulated first coil electrode at a distal portion thereof and an insulated coil portion proximal to the first coil electrode to provide an electrical connection between the first coil electrode and an electrical connector within the hub, the first coil electrode having a diameter larger than the proximal coil portion; and a distal portion of the channel member is uninsulated to provide a second coil electrode and the channel member comprises a lumen having a diameter larger than the diameter of the insulated coil portion of the first member, wherein the insulated collar is located between the first and second coil electrodes, and the insulated coil portion of the first member is located within the lumen of the channel member.

In at least some embodiments, the catheter probe comprises an insulated collar; a first member defining the catheter distal end, the first member comprising an uninsulated first coil electrode at a distal portion thereof and an insulated wire portion proximal to the first coil electrode to provide an electrical connection between the first coil electrode and a first electrical connector within the hub; and a distal portion of the channel member is uninsulated to provide a second coil electrode, the channel member comprises a lumen and the channel member is connected to a second electrical connector within the hub, wherein the insulated collar is located between the first and second coil electrodes, and the wire portion of the first member is located within the lumen of the channel member.

In at least some embodiments, the first coil electrode has a proximal portion with a smaller diameter than the uninsulated portion of the first coil electrode, the second coil electrode has a distal portion with a smaller diameter than the uninsulated portion of the second coil electrode and the insulated collar has an inner diameter such that inner portions of the insulated collar contact the smaller diameter portions of the first and second coil electrodes.

In at least some embodiments, the smaller diameter portions of the first and second coil electrodes are insulated.

In at least some embodiments, the catheter probe comprises first and second insulated members; a first member defining the catheter distal end, the first member comprising an uninsulated first coil electrode at a distal portion thereof and a first insulated wire portion proximal to the first coil electrode to provide an electrical connection between the first coil electrode and a first electrical connector within the hub; a second member also defining the catheter distal end, the second member comprising an uninsulated second coil electrode at a distal portion thereof and a second insulated tubular wire portion proximal to the second coil electrode to provide an electrical connection between the second coil electrode and a second electrical connector within the hub; and a distal portion of the channel member is uninsulated to provide a third coil electrode, the channel member comprises a lumen and the channel member is connected to a third electrical connector within the hub, wherein the first insulated member is located between the first and second coil electrodes, the second insulated member is located between the second and third coil electrodes, and the first and second wire portions are located within the lumen of the channel member.

In at least some embodiments, the hub is releasably attachable with a proximal portion of the catheter body, the proximal portion of the catheter body comprises at least one electrical contact and the hub comprises a corresponding at least one electrical contact that is adapted to electrically connect with the at least one electrical contact of the proximal portion of the catheter body when the hub is attached to the catheter body.

In at least some embodiments, the catheter probe further comprises at least one temperature sensor located near the at least one electrode, and there are at least two electrical contacts in the proximal portion of the catheter body and the hub that are electrically connected to the at least one electrode and the at least one temperature sensor respectively.

In at least some embodiments, the hub comprises a channel and the catheter body comprises a lumen defined by the channel member, the hub is adapted to releasably receive a stylet having a shaft and the channel and the lumen are sized to receive the shaft of the stylet.

In at least some embodiments, the channel member comprises at least two conductive surfaces spaced apart from one another on a distal portion of the channel member, a lumen and at least two electrical leads within the lumen that connect to the at least two conductive surfaces, the hub comprises at least two intermediate electrical connections that are connected to the at least two electrical leads; and the catheter distal end comprises at least two electrodes and an insulator ring positioned there between, the at least two electrodes being adapted to electrically engage the at least two conductive surfaces.

In at least some embodiments, the catheter probe further comprises at least two thermocouple sensors positioned within the lumen in close proximity to the at least two conductive surfaces.

In at least some embodiments, the at least one electrode comprises alternating insulated and uninsulated sections.

In at least some embodiments, the at least one electrode comprises a coil electrode comprising alternating uninsulated and insulated coils. In such cases, the coil electrode may comprise more insulated coils than uninsulated coils.

In at least some embodiments, the at least one electrode is partially circumferentially covered by an insulator such that the at least one electrode has an uninsulated portion defined by arc of a degrees.

In at least some embodiments, the channel member is adapted to provide a housing for the catheter distal end and a portion of the channel member is uninsulated to provide the at least one electrode, and wherein the hub comprises a channel to receive one of a stylet and a thermocouple catheter probe in use.

In another aspect, in at least one example embodiment described herein, there is provided a use of a catheter probe for therapeutic treatment of a target tissue region, wherein the catheter probe comprises a proximal hub comprising a hub housing and at least one wire; a catheter body connected to the proximal hub, the catheter body comprising a channel member and an insulator, the channel member being adapted to provide a housing for a portion of the catheter body and a conductive pathway, and the insulator being adapted to cover the channel member; and a catheter distal end comprising at least one electrode connected to the at least one wire. The use comprises placing the distal catheter end in close proximity to the target tissue region; applying a radiofrequency current to the at least one electrode to ablate a portion of the target tissue region; and measuring an impedance using the at least one electrode to determine effectiveness of the treatment.

In at least some embodiments, the use further comprises applying a stimulus current to the at least one electrode prior to applying the radiofrequency current to determine that the catheter probe is correctly located.

In at least some embodiments, the catheter probe further comprises a thermocouple probe and the use further comprises monitoring a temperature of the target tissue region before, during or after delivery of the radiofrequency current.

In at least some embodiments, the catheter probe further comprises a fluid injection port to receive a fluid in use and a plastic tubing to provide the fluid to an interior portion of catheter body and the use further comprises delivering a fluid to the target tissue region.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and in which.

DESCRIPTION OF VARIOUS EMBODIMENTS

Figure 1:
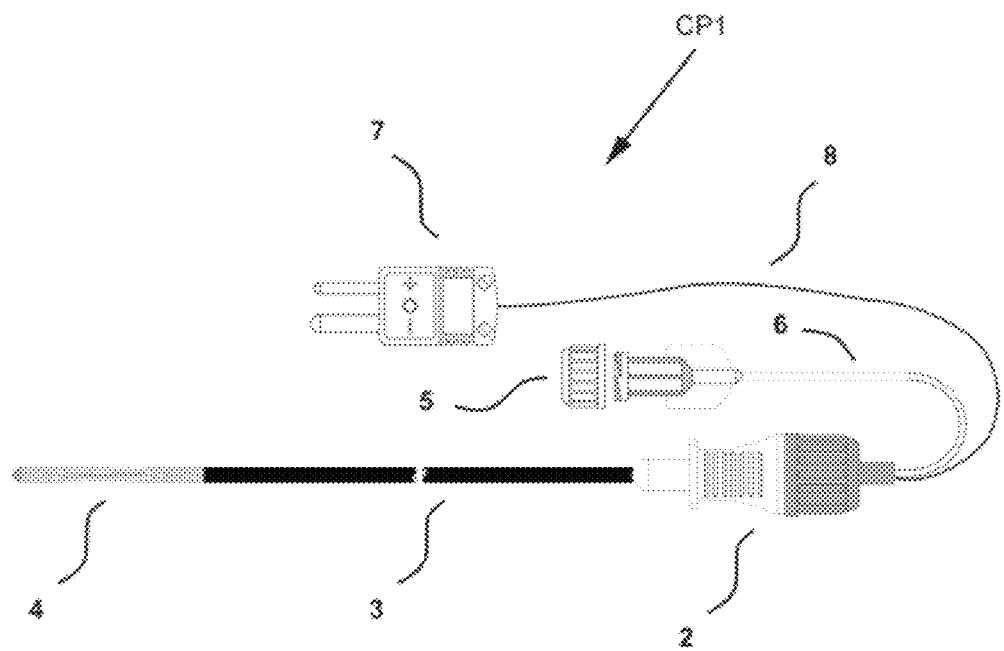
FIG. 1 shows an example embodiment of a multi-purpose catheter probe.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

It should be noted that the term "catheter probe" used herein is meant to represent a medical device that comprises at least some of the functionality of both a catheter and a probe. It should also be noted that the term "hub" used herein is meant to represent an element that can be used as a handle to hold the catheter probe as well as to provide electrical and fluid connections and the like. Furthermore, the term "distal" is used to generally indicate an element or portion of an element of a catheter probe that is located closer to the working end of the catheter probe and further away from the hub of the catheter probe. The term "proximal" is used to generally indicate an element or portion of an element that is located closer to the hub of the catheter probe and further away from the working end of the catheter probe. The term "working end" typically means the portion of the catheter probe that is first inserted into a patient and is also the portion of the catheter probe that provides various functions, such as at least one of fluid expulsion, RF ablation, temperature sensing and the like. Furthermore, all of the components described herein for the catheter probes are made from medical grade materials.

The various embodiments described herein generally relate to multi-purpose catheter probes that provide the functionality of catheters and probes for diagnostic and therapeutic purposes. The various multi-purpose catheter probes described herein generally provide elements for providing at least two of: passage of fluids into body cavities, electrical stimulation, electrical impedance measurement, temperature monitoring, and thermoablation. The various multi-purpose catheter probes described herein generally have a small diameter, and are flexible so that they are steerable to facilitate, and in some cases make uniquely possible, access to various regions such as but not limited to an epidural space, a spinal space, or a paravertebral space for diagnostic and therapeutic procedures to treat chronic neurogenic pain not relieved by more conservative methods. The various multi-purpose catheter probes described herein can also be used in other areas of a patient's body. Accordingly, the multi-purpose catheter probes described herein may make possible an enlarged range of applications at a greater number of locations as compared to conventional catheters and probes. In addition, the various embodiments of the multi-purpose catheter probe described herein are designed such that they may be constructed with a small diameter that allows for their incorporation within endoscopic probes. Furthermore, the various embodiments of the multi-purpose catheter probes described herein may be supplied, if so desired, as a packaged, sterilized, single use disposable product or alternatively as a sterilizable, reusable product.

An example embodiment of a multi-purpose catheter probe CP1 is shown in FIG. 1. The multi-purpose catheter probe comprises a proximal hub 2, a tubular catheter body 3, and a catheter distal end 4. The proximal hub 2 has a hub housing that is made of plastic, but it can be constructed out of other suitable non-conductive material or an appropriately insulated metal. The proximal hub 2 provides a handle area that allows a user to hold the catheter probe CP1. The tubular catheter body 3 is illustrated with a broken middle section to indicate that its length relative to other members is greater than shown. The tubular catheter body 3 and the catheter distal end 4 comprise a tightly wound continuous main coil 10 of surgical grade stainless steel (see FIG. 2) that has a smooth polymer coating, or other suitable insulator, over the tubular catheter body 3 but not over the catheter distal end 4 which is uninsulated. It should be understood throughout this description that stainless steel is but one type of material that can be used to implement the coil 10 and the coil 10 can also be made from titanium, nickel/titanium alloys (Nitinol) as well as various other medical grade metals as is known by those skilled in the art. Furthermore, other elements can be used other than the coil 10 such as, for example, a flexible metallic tube (this can apply to the other embodiments described herein). The main coil 10 provides a housing for the catheter body 3 and a conductive pathway (in other embodiments, the main coil 10 can provide at least a portion of the catheter body and in at least some cases a substantial portion of the catheter body 3). The tightly wound coil construction allows for the physical flexibility of the multi-purpose catheter probe CP1 while maintaining a 1:1 torque capability for guidance control. The length of the tubular catheter body 3 can typically be about 25 to 30 cm, but for certain applications it can be as short as 10 cm or less, or as long as 60 cm or more, and its outer diameter can typically be about 18 gauge (1.27 mm) to 20 gauge (0.91 mm). However, the catheter body 3 can have other dimensions as dictated by its particular application. Variations in length and diameter can be used according to the desired application. The length of the catheter distal end 4 can typically be about 10 mm, but is typically about 5 mm to 15 mm, although a range of about 2 mm to 25 mm or greater can also be used depending on the particular application.

A feature of this embodiment, as well as other embodiments described herein, is the multiplicity of functions that can be incorporated within the multi-purpose catheter probe CP1. This allows many functions to be executed without changing the position of the multi-function catheter probe CP1 or engaging in cumbersome replacement of functional modules.

(i) A first function of the multi-purpose catheter probe CP1 is as a catheter for the injection of fluids into body spaces and tissues by the inclusion of a fluid injection port 5 and a plastic tubing 6 connecting the fluid injection port 5 through the proximal hub 2 to an inner lumen of the tubular catheter body 3 formed by the inner wall of the stainless steel coil 10. The injected fluid exits at the catheter distal end 4 in a manner described in more detail below.

(ii) A second function of the multi-purpose catheter probe CP1 is as a probe for the application of an electrical stimulus to targeted tissue that is in contact with or close to the catheter distal end 4. An electrical lead within a flexible, multi-lead cable 8, connected via a connector plug 7 to an instrument with a variable electrical stimulus output, connects to the metallic structure of the tubular catheter body 3 within the proximal hub 2. This metallic structure serves as a conductive pathway to the uninsulated catheter distal end 4 which is guided to the target area during use. In this case, the catheter distal end 4 acts as an electrode. A stimulus response can be used to confirm the accuracy of the placement of the catheter distal end 4 before therapeutic procedures are initiated, or stimulus current can be used for short or long term therapeutic benefit such as the alleviation of chronic spinal pain.

(iii) A third function of the multi-purpose catheter probe CP1 is as a probe for the application of ablation energy, as a continuous or pulsed RF (radiofrequency) current for example, that is provided to the targeted tissue which is in contact or close proximity with the catheter distal end 4. In this case, the catheter distal end 4 also acts as an electrode. The same electrical lead (as used in (ii) above to carry stimulus current) within the flexible multi-lead cable 8, connected to an instrument with an RF current output, connects to the metallic structure of the tubular catheter body 3 within the proximal hub 2 which, as in (ii) above, serves as a conductive pathway (but now for RF current) to the uninsulated catheter distal end 4 which is in contact or close proximity with a target area during use. A conventional, large area, electrically conductive pad can be placed, for example, on an arm or leg to serve as a return path for the electrical stimulation or ablation current that is injected into the body via the catheter distal end 4 during use.

Figure 2:
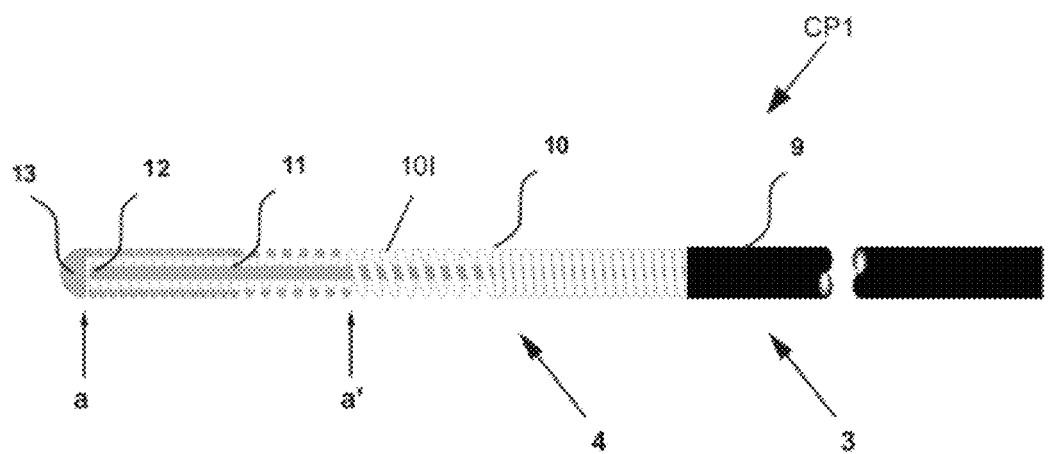
FIG. 2 shows a detailed view of a catheter distal end of the multi-purpose catheter probe of FIG. 1.
Figure 3:
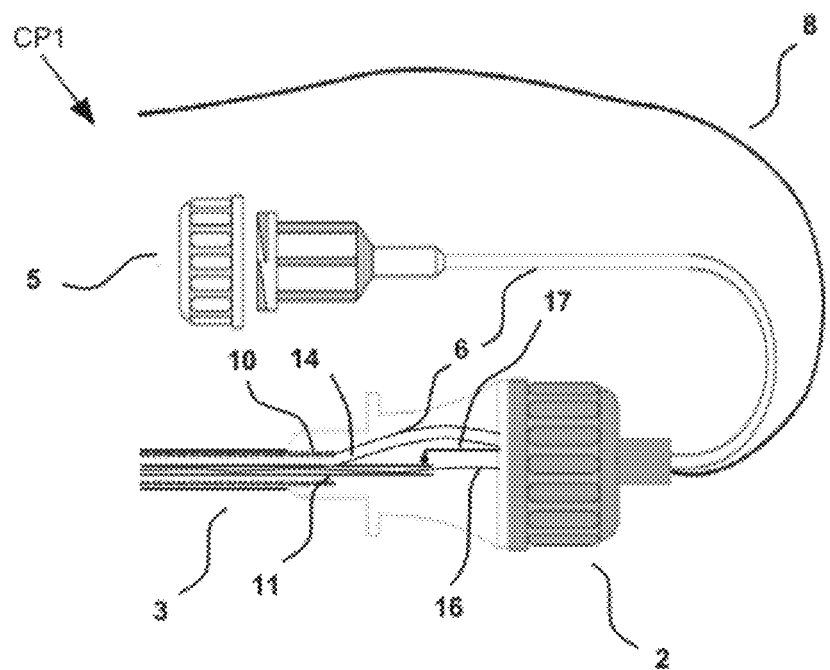
FIG. 3 shows a detailed view of connections within a proximal hub at a proximal end of the multi-purpose catheter probe of FIG. 1.

(iv) A fourth function of the multi-purpose catheter probe CP1 is as a means for measuring electrical impedance of tissue or fluids at the catheter distal end 4 when the multi-purpose catheter probe CP1 is connected to an instrument with an impedance measurement module. Impedance values can be used, for example, as a confirmation of the location of the catheter distal end 4 (e.g. very low values indicate fluid rather than tissue) or for assessing the effectiveness of an RF ablation procedure (e.g. high values indicate thermocoagulation). Once again, the catheter distal end 4 acts as an electrode (v) A fifth function of the multi-purpose catheter probe CP1 is a means for monitoring tissue temperature. A very small diameter tubular thermocouple probe, described in association with FIGS. 2 and 3, is positioned within the lumen of the tubular catheter body 3 and the catheter distal end 4. A thermocouple member, inside the thermocouple probe, is positioned at a predetermined location within the length of the catheter distal end 4 to measure a change in tissue temperature related to the application of, for example, pulsed RF stimulation or RF ablation energy. The thermocouple probe is connected to a temperature measuring instrument via two leads within the flexible multi-lead cable 8 in a manner described below.

It should be noted that there can also be other embodiments of the multi-purpose catheter probe CP1 in which certain structures are included or excluded such that these other embodiments provide any combination of the above-noted functions.

The electrical stimulation function of the multi-purpose catheter probe CP1 can be used in a number of beneficial manners. It can be used in a low frequency mode, for example 1 Hz to 100 Hz, to identify adjacent sensory structures, as well as ensuring that the probe is not adjacent to motor structures. Electrical stimulation can also be used prior to therapy to establish a benchmark for assessing results following therapy. For example, stimulation for at least one of the frequencies: 2,000 Hz (for Aβ fibers), 250 Hz (for Aδ fibers) and 5 Hz (for C fibers) can be performed using current perception threshold and intensity of pain as outcome metrics. As well, the application of pulsed RF energy to a nerve, a nerve root, a nerve ganglion, or a part of the spinal cord can be used therapeutically to relieve chronic pain.

The availability of an RF ablation function also makes possible the use of the various multi-purpose catheter probes described herein in association with a procedure called spinal endoscopic adhesiolysis for the removal of fibrotic barriers in the epidural space. Endoscopic adhesiolysis is usually achieved mechanically by a tearing action at the tip of an epiduroscope. It is performed because of the belief that epidural fibrosis prevents drugs from reaching the target areas. Adhesiolysis has also been performed to a limited extent with RF current ablation as a means to clean up remaining fibrotic areas not adequately removed by mechanical resection.

Impedance measurement, as made available by the various multi-purpose catheter probes described herein, assists in the confirmation of the location of the catheter distal end 4 by comparing results with known impedance values of different tissues and of fluids. It also serves as a means for assessing, together with temperature rise, the effectiveness of an RF ablation procedure. No impedance change is indicative of an ineffective lesion, whereas lower or higher impedance values indicate tissue liquefaction or coagulation respectively.

Temperature monitoring, as made available by the various multi-purpose catheter probes described herein, is important for ensuring the safety of a number of the applications with which these catheter probes can be used. For example, temperature rise during pulsed RF treatment can be regulated not to exceed 42° C. to avoid thermal damage to tissue.

Such multiplicity of functions allows the multi-purpose catheter probes described herein to be used with a suitably multi-functional instrument which incorporates electrical stimulation, temperature monitoring, impedance measurement, and RF ablation current modules within a single instrument FIG. 2 shows the details of the catheter distal end 4. A short length of the adjacent part of the tubular catheter body 3 is also shown. An insulator 9, such as a polymer coating, covers the tubular catheter body 3 and terminates at the catheter distal end 4, revealing a stainless steel coil 10, which can act as an electrode. The stainless steel coil 10 is tightly wound along a substantial portion of its length, and in some cases its entire length, except over a portion of the catheter distal end 4 where it is more loosely wound, here shown in its middle section, where the coil 10 also acts as an electrode. The coil 10 extends along a substantial portion, and in some cases along the entire length, of the catheter body 3 to provide the catheter probe CP1 with flexibility. The more loosely wound portion 101 allows fluid injected into the tubular catheter body 3 to flow into surrounding tissue or body space during use.

For purposes of illustration, a hemi-circumferential section a-a' of the stainless steel coil 10 has been removed to more clearly reveal the lumen of the coil 10 which contains a tube 11, which, for this example, is a 30 gauge (0.31 mm) stainless steel tube. The stainless steel tube 11 contains at its tip a thermocouple junction 12 at which point there is an electrical connection between a wire of the multi-lead wire 8 and the stainless steel tube 11 (the wire is within the tube 11 and is not shown in FIG. 2). The diameter of the stainless steel tube 11 can be larger or smaller, depending on the application. For example, the tube 11 can be used to provide stiffness, and if needed, a preferential bending (see FIGS. 6A-6B) in which case it has to be sufficiently strong. However, in applications where the catheter probe allows for liquid injection into surrounding tissue, the tube 11 should be sized such that there is a large enough gap to allow liquid to freely flow between the outer diameter of the tube 11 and the inner diameter of the coil 10. The stainless steel tube 11 extends from the proximal hub 2 to the catheter distal end 4 and comprises an end portion that is spaced apart from a rounded, atraumatic end 13 of the catheter distal end 4. In other embodiments, the end 13 can be tapered or pointed depending on the application. For example, the end 13 can be pointed enough to allow the use of the end 13 to puncture a hole or create a channel in surrounding tissue but not to cut/damage surrounding vessels or nerves. Furthermore, in alternative embodiments, the thermocouple junction 12 can be positioned at other locations within the stainless steel tube 11 to sense tissue temperature at other locations such as, for example, at the central portion of the catheter distal end 4. The tube 11 also conducts electrical signals between the connector plug 7 and the catheter distal end 4 which acts as an electrode.

Referring now to FIG. 3, an insulated wire 16, such as constantan for example, passes through the stainless steel tube 11 until it connects with the inner wall of the stainless steel tube 11 at the catheter distal end 4 to form the thermocouple junction 12 which is a hot thermocouple junction near the electrode portion of the catheter probe CP1 although other locations can also be chosen. The stainless steel tube 11 then serves as a conductive path back to the interior of the proximal hub 2 where the wall of the stainless steel tube 11 connects to a lead wire 17, which can be made from copper for example, of the multi-lead cable 8. The lead wire connects at its other end to form a cold thermocouple junction within a multi-functional instrument that contains a temperature monitoring module. In this manner, only one wire is required within the lumen of stainless steel tube 11, which allows for the implementation of very small diameter thermocouple probes for the various embodiments of the multi-purpose catheter probe described herein. Although constantan and copper are used here for the thermocouple junction, other metal pairs well known to the industry such as nickel-chromium and nickel can also be used.

Another feature of the various embodiments of the multi-purpose catheter probe described herein is that the flexibility of the tubular catheter body 3 and the catheter distal end 4 is not compromised by the division of the lumens of these elements into compartments to accommodate interior members, as is common in conventional catheters. This is because in the various embodiments of the multi-purpose catheter probe described herein only a single lumen is required. The single lumen is defined by the coil 10 which extends along a substantial portion of the catheter body 3.

FIG. 3 also provides details about connections within the proximal hub 2 of the multi-purpose catheter probe CP1. Part of the outer wall of the proximal hub 2 and the tubular catheter body 3 has been removed to reveal inner components. The plastic tubing 6 extends from the fluid injection port 5 into the hub 2. Fluids injected into the fluid injection port 5 flow through the plastic tubing 6 which is connected to an opening 14 of the stainless steel coil 10 of the tubular catheter body 3. The opening 14 is defined by the inner surface of the coil 10 and the outer surface of the tube 11. In use, injected fluid flows distally between the inner wall of stainless steel coil 10 and the outer wall of the stainless steel tube 11 to the exit point at the loosely wound portion 101 of the stainless steel coil 10 at the catheter distal end 4.

Referring still to FIG. 3, an electrical lead 17 from the flexible multi-lead cable 8 is connected to the stainless steel tube 11 to form a conductive path for electrical stimulus current or RF ablation current (not simultaneously) to the catheter distal end 4, which is the uninsulated portion of the stainless steel coil 10. The conductive path from the stainless steel tube 11 to the stainless steel coil 10 in the catheter distal end 4 is the surface contact between the outer wall of the stainless steel tube 11 and the inner wall of the stainless steel coil 10. The electrical lead 17 has a higher current-carrying capacity than other leads in the multi-lead cable 8. A fine electrical lead 16 is used to complete the thermocouple probe and may comprise constantan wire. The diameter of the electrical lead 16 is small enough to allow it to be placed within the tube 11.

Figure 4:
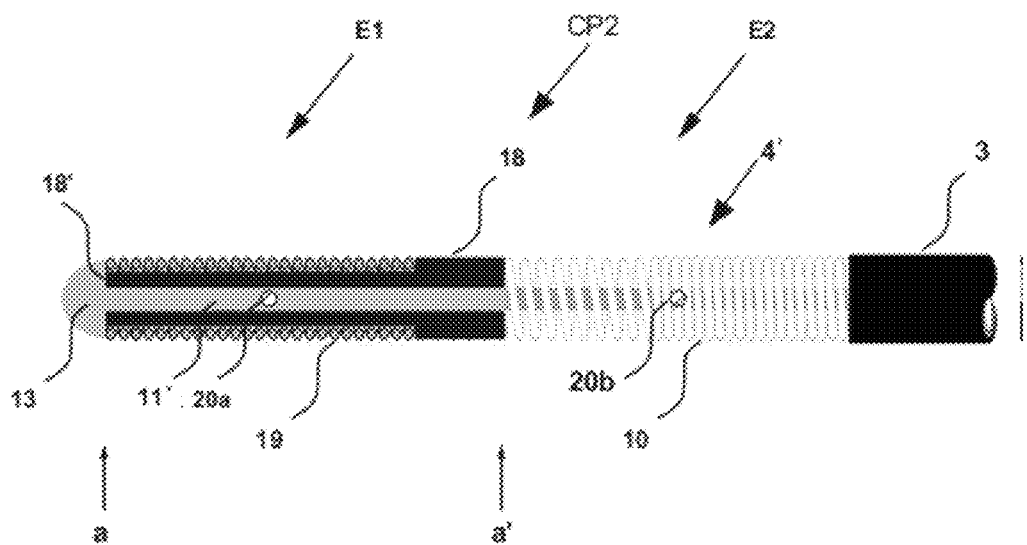
FIG. 4 shows another example embodiment of a multi-purpose catheter probe in which the catheter distal end is configured for bipolar stimulation and ablation.

Another example embodiment of a multi-purpose catheter probe CP2 provides bipolar electrical stimulation and/or bipolar RF ablation to a region of tissue for applications where highly localized stimulation or ablation effects are required. FIG. 4 shows a portion of the tubular catheter body 3 and an adjacent portion of the catheter distal end 4' for the multi-purpose catheter probe CP2. In this example embodiment, the catheter distal end 4' is divided into first and second sections with uninsulated flexible stainless steel coils serving as electrodes E1 and E2 which are separated by a cylindrical insulator 18. The cylindrical insulator 18 has a proximal portion and a distal elongated portion with a smaller outer diameter than that of the proximal portion. As in the previous embodiment, the flexible stainless steel coil 10 provides a housing and a conductive pathway for the catheter probe CP2. The coil 10 has a distal portion that is uninsulated and is used as an electrode E2 in the catheter distal end 4' and has tightly and loosely wound portions, the latter serving as an exit region for ejecting fluids into nearby tissue during use. If desired, all of the electrode E2 could be loosely wound and still retain its other functions. Although the electrodes E1 and E2 of the multi-purpose catheter probe CP2, or the single electrode of the multi-purpose catheter probe CP1, are described as being comprised of stainless steel coils, they could alternatively be fabricated from conductive cylindrical shells, a series of interconnected conductive cylindrical rings, or other configurations.

As in FIG. 2, a hemi-circumferential section a-a' of the catheter distal end 4' has been removed to more clearly reveal in FIG. 4 the second stainless steel coil 19 wrapped around or otherwise located on the elongated flexible section 18' of cylindrical insulator 18. In an alternative, the coil 19 may be slidably received. The coil 19 serves as the electrode E1. The cylindrical insulator 18 and its extended portion 18' in turn tightly envelope the stainless steel tube 11' to securely hold the electrode E1 in place. The stainless steel tube 11', which in this embodiment is insulated, terminates with a rounded, atraumatic, conductive end portion 13. The conductive end 13 and the cylindrical insulator 18 form first and second end limits for the coil 19, which can be made from stainless steel. The conductive end 13 is electrically continuous with the coil 19 by at least one of direct physical contact and by electrical connection. In this manner, the inner wall of the insulated stainless steel tube 11' provides a conductive pathway for the connection of the coil 19, comprising electrode E1, to an electrical stimulus or RF ablation current source, while the outer wall of the tube 11' is insulated. And as previously described for the multi-purpose catheter probe CP1, the stainless steel coil 10 extends within the tubular catheter body 3 and provides a conductive pathway for the electrode E2. The catheter body 3 is insulated and in at least some cases may have a polymer coating. Accordingly, in this manner, the multi-purpose catheter probe CP2 provides a bipolar electrode configuration for the application of an electrical stimulus or RF ablation current via the electrodes E1 and E2.

The multi-purpose catheter probe CP2 also comprises two temperature sensors 20a and 20b situated within the stainless steel tube 11'. The temperature sensor 20a is positioned within or near the electrode E1 and the temperature sensor 20b is positioned within or near the electrode E2. The temperature sensors 20a and 20b can be thermocouples, but other sensors such as thermistors, and the like may also be used. In this example embodiment, each temperature sensor 20a and 20b has an electrical lead (not shown) routed within the stainless steel tube 11'.

Figure 5:
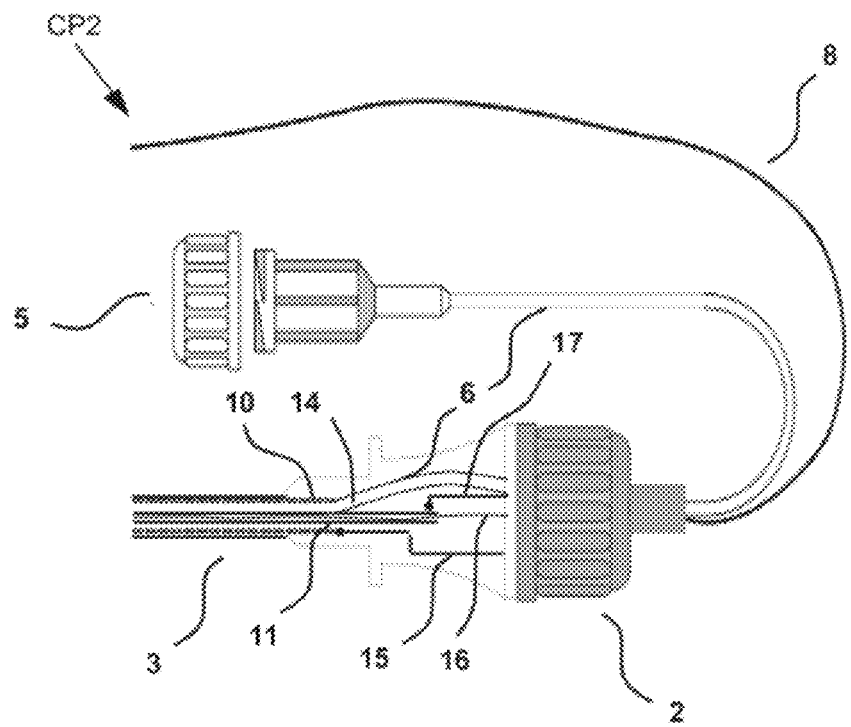
FIG. 5 shows a detailed view of connections within the proximal hub at the proximal end of the multi-purpose catheter probe of FIG. 4.

Referring now to FIG. 5, shown therein is a detailed view of the connections within the proximal hub 2 for the multi-purpose catheter probe CP2. Part of the outer wall of the proximal hub 2 and the tubular catheter body 3 has been removed to reveal the inner components. This design is similar to that of multi-purpose catheter probe CP1 shown in FIG. 3, except for an extra electrical lead 15 that is connected to the coil 10 to provide an electrical signal to the electrode E2.

Figure 6A:
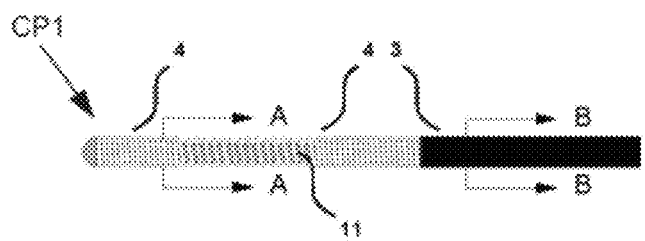
FIG. 6A shows another example embodiment of a multi-purpose catheter probe in which the shape of a portion of the catheter probe has been altered to impart a directional preference to the movement of the catheter probe.
Figure 6B:
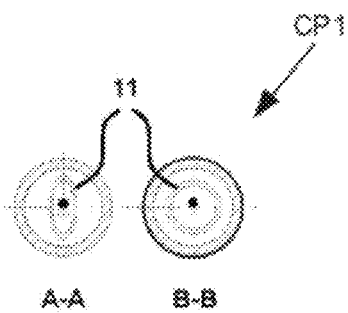
FIG. 6B shows sectional views through the distal end and adjacent tubular body of the multi-purpose catheter probe of FIG. 6A.

The multi-purpose bipolar electrode catheter probe CP2 has the same multiplicity of functions as the multi-purpose single electrode catheter probe CP1. Both of these catheter probes CP1 and CP2 can have, in general, the same dimensions and flexibility to provide access to tissue targets that is not possible with conventional catheters and probes having larger diameter or less flexibility. The ability to guide these multi-purpose catheter probes CP1 and CP2, including the other embodiments described herein, to a tissue target or fluid space can be enhanced if required as shown in FIGS. 6A-6B, which shows a modified version of the multi-purpose catheter probe CP1 as an example. FIG. 6A shows the catheter distal end 4 and an adjacent section of the tubular catheter body 3. Sections A-A and B-B, taken through the catheter distal end 4 and the tubular catheter body 3 respectively, are shown in FIG. 6B. In section B-B, the stainless steel tube 11 is circular, whereas in section A-A it is compressed to a non-circular shape with minor and major axes. This imparts a directional preference in the extended direction of the minor axis.

Figure 7A:
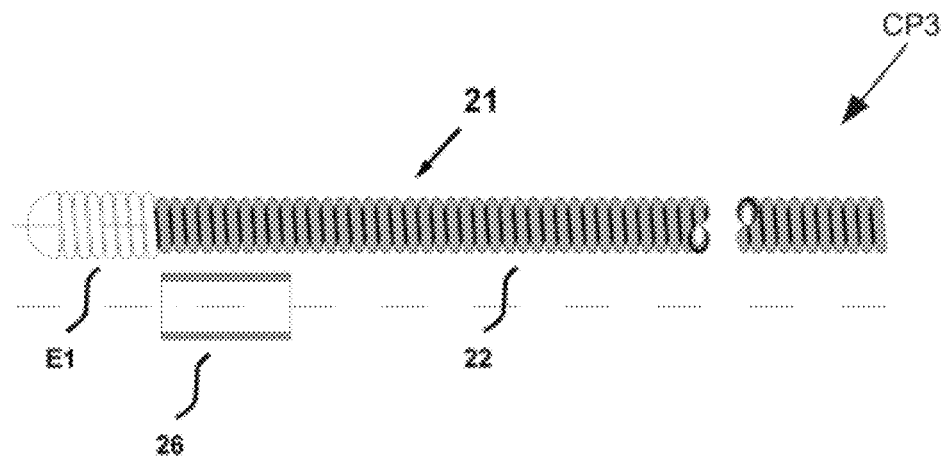
FIGS. 7A-C show detailed views of another example embodiment of a multi-purpose catheter probe which uses a different construction from that illustrated in FIG. 4 to obtain a catheter distal end configured for bipolar stimulation and ablation.
Figure 7B:
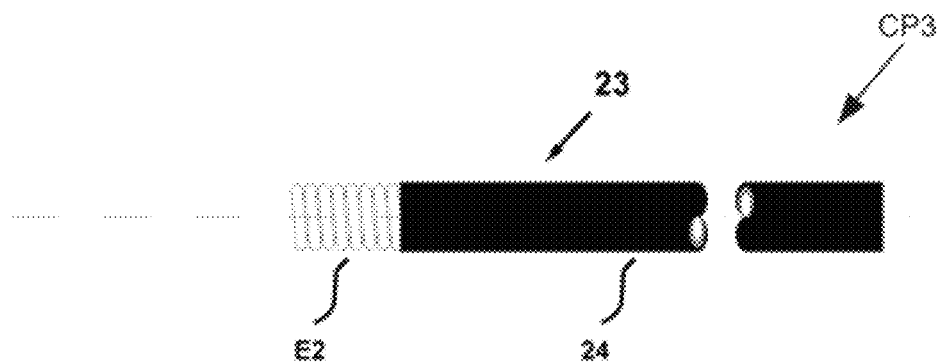
Figure 7C:
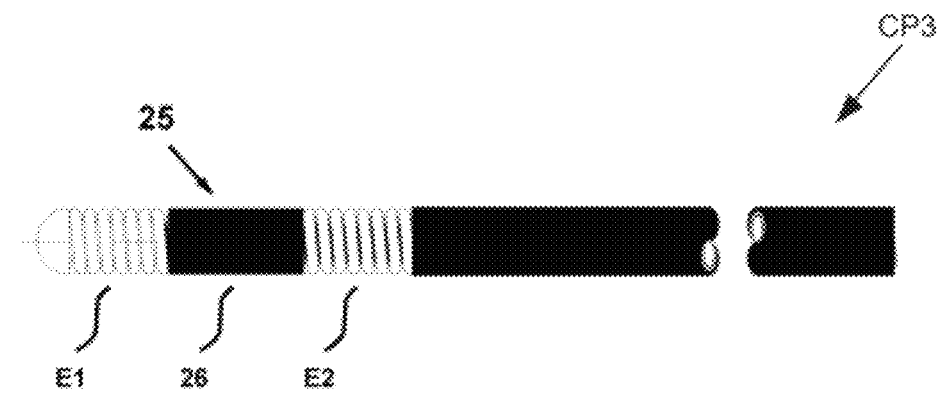

Referring now to FIG. 7A shown therein is an alternative example embodiment of a portion of a multi-purpose catheter probe CP3 having a bipolar electrode configuration. The distal catheter end of the multi-purpose catheter probe CP3 is constructed from two members. A first member 21 is a tightly wound continuous coil of surgical grade stainless steel with a first diameter and an uninsulated distal section that provides the electrode E1, and a longer, insulated proximal section 22 with a second diameter that is smaller than the first diameter. The section 22 continues to the hub (not shown) of the multi-purpose catheter probe CP3 to provide an electrical connection between the electrode E1 and an electrical connector within the hub (not shown). A second member 23, shown in FIG. 7B, again comprises a tightly wound continuous coil of surgical grade stainless steel with a roughly constant diameter that is approximately equal to the larger diameter of the distal section of the first member 21 that provides the electrode E1. The distal section of the second member 23 is uninsulated to provide the electrode E2. The longer proximal section 24 of the second member 23, which continues to the hub (not shown) of the multi-purpose catheter probe CP3, is insulated. Accordingly, in this embodiment, there are two coils that are concentric and extend along a substantial portion of the catheter body of the multi-purpose catheter probe CP3 and provide a housing and conductive pathways. The insulation used in this embodiment can be a polymer or other suitable material. The inner diameter of the stainless steel coil E2 of the second member 23 and the inner diameter of an insulated collar 26 (see FIG. 7A) is slightly greater than the outer diameter of the insulated proximal section 22 of the first member 21. This allows the insulated collar 26 and the second member 23 to slide over the first member 21 and form, as shown in FIG. 7C, the bipolar distal end 25 of the multi-purpose catheter probe CP3. Accordingly, the multi-purpose catheter probe CP3 comprises electrodes E1 and E2 that are separated by the insulated collar 26. A portion or all of the electrodes E1 and/or E2 can be more loosely wound to allow for infusion of fluid into the surrounding tissue or body space during use. The multi-purpose catheter probe CP3 can also comprise thermocouples, or other temperature sensors, to sense tissue temperature. The thermocouples can be variably positioned within the electrodes E1 and E2 or elsewhere to sense tissue temperature at a desired location. For example, temperature sensors can be positioned within the electrodes if the coils are wound out of tubes or other elements with a hollow profile. Alternatively, a single thermocouple probe (such as the one shown in FIG. 2 using the tube 11) with multiple temperature sensors can be inserted into the inner diameter of the coil 22. In another alternative, multiple thermocouple probes of various lengths with single sensors can be inserted into the inner diameter of the coil 22.

Referring now to FIGS. 8A-8D, shown therein is an example embodiment of a tripolar electrode configuration for a multi-purpose catheter probe CP4. The distal end of the multi-purpose catheter probe CP4 is generally constructed from three members. A first member 27 (see FIG. 8A) has at its distal end a tightly wound continuous coil of surgical grade stainless steel which comprises a larger diameter, uninsulated distal section that provides an electrode E1 and a smaller diameter, proximal section 28 (which can be insulated or uninsulated) from which member 27 continues in a straight, insulated wire 29 that makes an electrical connection with a first electrical connector within the hub (not shown) of the multi-purpose catheter probe CP4. A second member 30, shown in FIG. 8B, has at its distal end a tightly wound continuous coil of surgical grade stainless steel which comprises a smaller diameter, distal and proximal end sections 31 (which can be insulated or uninsulated) separated by a larger diameter, uninsulated middle section that provides an electrode E2. The diameter of the insulated end sections 31 can be approximately equal to the diameter of the proximal, insulated section 28 of the first member 27, and the diameter of the uninsulated middle section that provides the electrode E2 can be approximately equal to the diameter of the distal uninsulated section of member 27 that provides the electrode E1. The proximal insulated end section 31 of the second member 30 continues as a straight, insulated wire 32 that makes an electrical connection with a second electrical connector within the hub (not shown) of the multi-purpose catheter probe CP4. The first and second members 27 and 30 can be constructed such that wires 29 and 32 are side by side. A third member 34, shown in FIG. 8C, comprises in its entirety, or a substantial portion thereof, a tightly wound continuous coil of surgical grade stainless steel which has a smaller diameter, distal end section 35 (which can be insulated or uninsulated), with the remainder of the coil being larger in diameter and approximately equal to the diameters of the distal uninsulated section of member 27 that provides the electrode E1 and the middle uninsulated section of member 30 that provides the electrode E2. The proximal portion of the third member 34 can be provided in a similar fashion as the coil 10 and therefore also provides a housing and a conductive pathway for the catheter probe CP4. The diameter of section 35 can be approximately equal to that of sections 31 of member 30 and the proximal section 28 of member 27. The distal section of member 34 that provides the electrode E3 is uninsulated, and the remaining proximal section 36 of member 34 is insulated and continues within the multi-purpose catheter probe to the hub (not shown) where it makes an electrical connection with a third electrical connector. The insulation used in the construction of the tripolar multi-purpose catheter probe CP4 can be a polymer or other suitable material. There can be some embodiments in which the electrodes E1, E2 and E3 are sized differently from one another either in terms of length or diameter (this may also apply to the other embodiments of the catheter probes described herein). It should be noted that the term electrical connector as used herein includes elements such as electrical contacts.

Figure 8A:
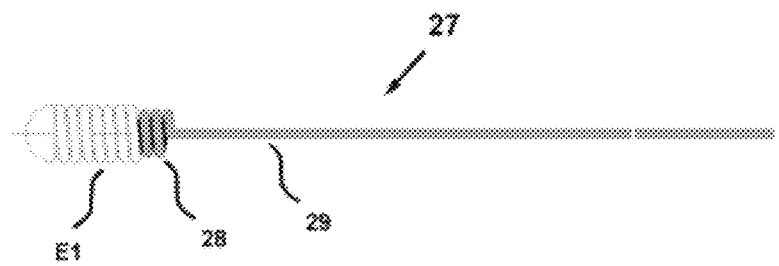
FIGS. 8A-8D show detailed views of another example embodiment of a multi-purpose catheter probe in which the catheter distal end is configured for tripolar stimulation and ablation.
Figure 8B:
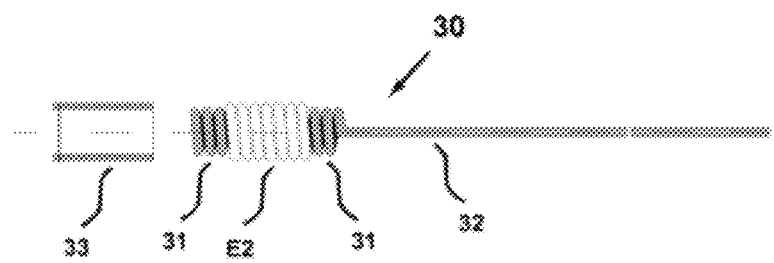
Figure 8C:
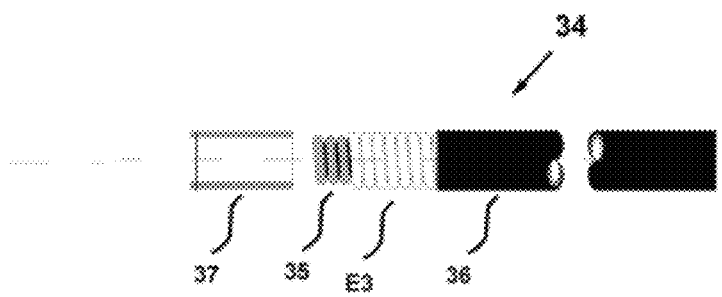
Figure 8D:
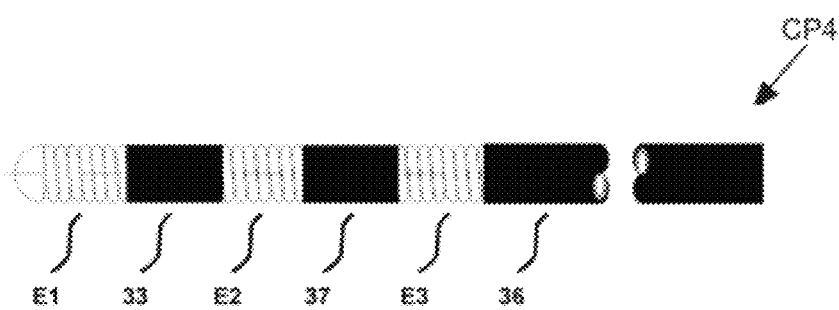

The inner diameter of the insulated collars 33 and 37 (see FIGS. 8B and 8C respectively), is slightly greater than the outer diameter of the smaller diameter coil sections of members 27, 30 and 34 such that inner portions of the insulated collars 33 and 37 contact the smaller diameter portions of the members 27, 30 and 34. Construction of the tripolar electrodes E1, E2, and E3, as illustrated in FIG. 8D, is obtained by the following steps: sliding the insulated collar 33 over the insulated wire 29 and the insulated proximal section 28 of the member 27; sliding the member 30 over the insulated wire 29 of the member 27 until the distal end section 31 of the member 30 is within the insulated collar 33; sliding the insulated collar 37 over the insulated wires 32 and 29 and the proximal end section 31 of the member 30; and then finally sliding the member 34 over the insulated wires 32 and 29 until the distal end section 35 of the member 34 is within the insulated collar 37.

Portions or substantially all of the electrodes E1, E2, and E3 can be more loosely wound to allow for the infusion of fluid into surrounding tissue or body spaces during use. In addition, thermocouples or other heat sensors for monitoring tissue temperature can be variably positioned within the electrodes E1, E2, and E3, or elsewhere in the multi-purpose catheter probe CP4, to sense tissue temperature. The sensors can be positioned within at least one of the electrodes E1, E2 and E3 in at least some cases. Alternatively, a single thermocouple probe with multiple sensors can be inserted into the inner diameter of at least one of the coils. Alternatively, thermocouple probes or various lengths with single sensors can be inserted within the inner diameter of at least one of the coils.

It should be noted that the coils that make up the electrodes E1, E2 and E3 can be wound out of tubes or other elements with a hollow profile. It should be noted that the profile does not have to have a round shape. Furthermore, it should be noted that the cross-section of any coils, the cross section of any wires and the cross-section of any catheters described herein are not limited to a circular shape. In addition, the cross-section of any catheters described herein can be circular in some portions and oval, D-shaped, rectangular, and the like in other portions to achieve the preferential bending of certain sections of the catheter.

In an alternative construction, the electrodes E1, E2, and E3 can be entirely uninsulated, i.e. there are no insulated sections 28, 31, and 35 respectively. Instead, insulator beads, or the like, with a central perforation, are slid over insulated wires 29 and 32 before assembly of the members 27, 30, and 34 into the tripolar electrode configuration. A sufficient amount of insulator beads are used to prevent electrical contact between the electrodes E1, E2 and E3. The insulator beads can also be adapted to allow the flow of injected fluid around them for exit at the catheter distal end. In another alternative, the insulated collars can have an outer diameter that is larger than the electrodes E1, E2 and E3 and collars that are countersunk on each end to accommodate the outer diameter of the electrodes E1, E2 and E3. In another alternative, the outer diameter of the insulated collars and the electrodes E1, E2 and E3 can be the same except at the end of the insulated collars where they make contact with an electrode, in which case the outer diameter of the insulated collar is reduced such that the inner diameter of an adjacent electrode is slightly greater than the outer diameter of the reduced end of the insulated collar thereby allowing for a uniform diameter when the insulated collars are assembled with the coil electrodes. In another alternative where there are no fluid injection capabilities, the insulated beads can have an inner diameter that is just larger than the straight wire portions 29 and 32 to hold the insulated beads in place.

The method of construction of the tripolar, multi-purpose catheter probe CP4 can be extended to allow for the assembly of other catheter probes with a multiplicity of electrodes, such as two, three, four or more electrodes, which are each separated by insulated collars or insulator beads as the case may be. Since this method of construction does not limit the length of the electrodes or the insulated collars (i.e. each can be as short or long as desired), multi-polar, multi-purpose catheter probes of different configurations can be produced for use for specific applications or within unusual anatomic structures. Furthermore, the described construction can also be beneficially applied to single purpose probes or catheter probes, such as, for example, those used only for stimulation or RF ablation.

Figure 9A:
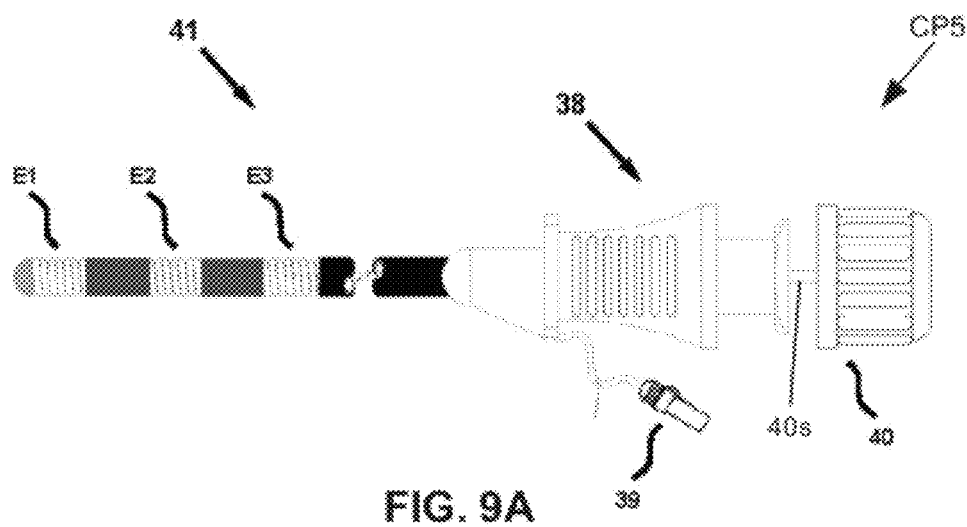
FIGS. 9A-C show detailed views of another example embodiment of a multi-purpose catheter probe which is constructed in two detachable parts so that one part can be implanted within a patient's body.
Figure 9B:
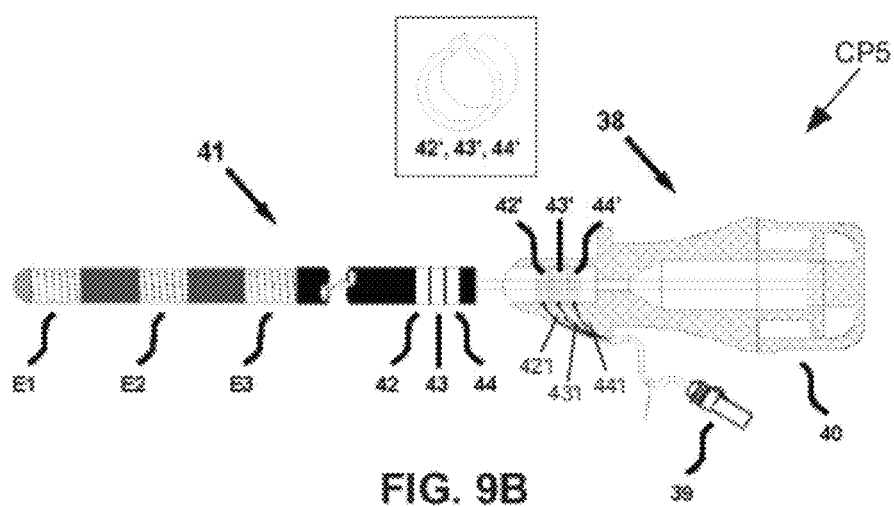
Figure 9C:
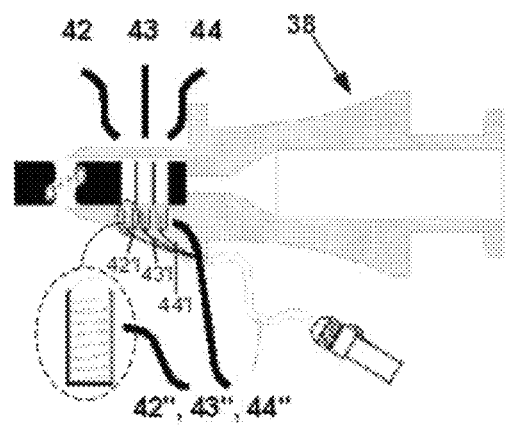

In another alternative, the multi-purpose catheter probes described herein can generally be constructed in two detachable parts: a catheter probe section and a detachable hub section. The hub section is releasably attachable with a proximal portion of the catheter probe section which defines a proximal portion of the catheter body. For example, in a tripolar electrode configuration, the multi-purpose catheter probe CP4 can be constructed as shown in FIGS. 9A-9C as multi-purpose catheter probe CP5 with a catheter probe section 41 defining the distal end of the catheter probe and including the electrodes E1, E2, and E3, and a detachable hub section 38. A majority of the proximal portion of the catheter probe section 41 can be formed from a coil such as the coil 10 to provide a housing and a conductive pathway for the catheter probe CP5. The proximal portion of the catheter probe section 41 contains electrical contacts or metal rings 42, 43, and 44, shown in FIG. 9B, which connect to the electrodes E1, E2, and E3 respectively. FIG. 9B also shows a section through the detachable hub 38, revealing electrical contacts or conductive surfaces 42', 43', and 44' which make contact with the metal rings 42, 43, and 44 respectively when the catheter probe section 41 is connected to the detachable hub section 38. It should be noted that the connections shown in FIGS. 9B-9C are just examples of the various ways to achieve an electrical connection between two conductive surfaces; other techniques to achieve an electrical connection may also be used. The number of electrical contacts for the probe section 41 and the detachable hub 38 depend on the number of electrodes and temperature sensors used in the catheter probe CP5 and can be as few as one contact for just one electrode or two contacts for one electrode and one temperature sensor. The inset in FIG. 9B shows that the conductive surfaces 42', 43' and 44' can be, for example, C-shaped contacts although other types of contacts can also be used as is known by those skilled in the art. Leads 42'I, 43'I, and 44'I from the conductive surfaces 42', 43', and 44' electrically connect the conductive surfaces 42', 43' and 44' to corresponding electrical contacts (not shown) in the connector plug 39. The connector plug 39 is connected to an instrument that can provide and/or receive electrical signals from the multi-purpose catheter probe CP4 during use. FIG. 9C provides another example embodiment for providing an electrical connection between the metal rings 42, 43, and 44 and the detachable hub section 38. In this example, spring loaded ball contacts 42", 43", and 44" make an electrical connection between the metal rings 42, 43 and 44 and the electrical leads 42'I, 43'I and 44'I. There are also leads that extend from the metal rings 42, 43 and 44 and travel within the catheter probe section 41 to the electrodes E1, E2 and E3. If the construction shown in FIGS. 8A-8D is used for the catheter probe section 41, then wires 27 and 32 are extended to and terminated at contacts 42 and 43. Once again, temperature sensors can be positioned within the electrodes if the coils are wound or are tubes. Alternatively, a single thermocouple probe (such as the one shown in FIG. 2 using the tube 11) with multiple temperature sensors can be inserted into the inner diameter of the coils. In another alternative, multiple thermocouple probes of various lengths with single sensors can be inserted into the inner diameter of the coils.

In alternative embodiments, additional metal rings on the catheter probe section 41 and additional conductive surfaces in the detachable hub 38 can be employed to incorporate other functions such as, for example, thermocouple temperature sensors positioned at or near the electrodes E1, E2, and E3.

The multi-purpose catheter probe CP5 is advantageous for implanting the catheter probe section 41 over periods of time in body spaces or tissues in applications where, for example, it is desired to periodically inject or continuously infuse medications for the relief of pain. The catheter probe section 41 can be made small with an essentially uniform diameter to make it possible to pass it through a cannula that was previously guided to the target body region, and then the cannula can be withdrawn over the catheter probe section 41 leaving all or a major portion of the catheter probe section 41 implanted in the target body region. In at least some cases where all of the catheter probe section 41 is implanted in the target body region, a pump that is used for fluid infusion can also be implanted. The pump can, for example, be implanted subcutaneously where it connects to an infusion port of the catheter probe section 41. Energizing the pump can be controlled, for example, by magnetic induction from a closely coupled external signal activating an on/off receiver/switch component of the pump.

FIG. 9A also shows a stylet 40 that is partially withdrawn from the detachable hub section 38. The stylet 40 has a long shaft 40s that is inserted within a channel in the detachable hub section 38 and a lumen of the catheter probe section 41. The lumen is comprised of the inner diameter of electrodes E1, E2 and E3 and the catheter probe body of section 41. This channel and lumen are sized to receive the shaft 40s of the stylet 40. The stylet 40 is typically used when repositioning the catheter probe section 41 as well as to provide the required stiffness and preferential bending, if needed, and can also be used to prevent any tissue from clogging its lumen. Once the catheter probe section 41 is properly positioned, the stylet 40 is completely withdrawn to allow for the injection of fluids or the insertion of a probe for temperature monitoring and/or delivery of electrical current.

Figure 10A:
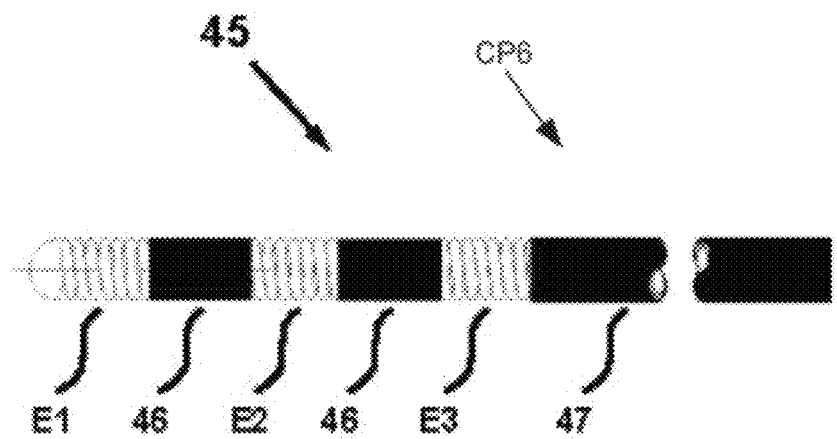
FIGS. 10A-C show detailed views of another example embodiment of a tripolar multi-purpose catheter probe.
Figure 10B:
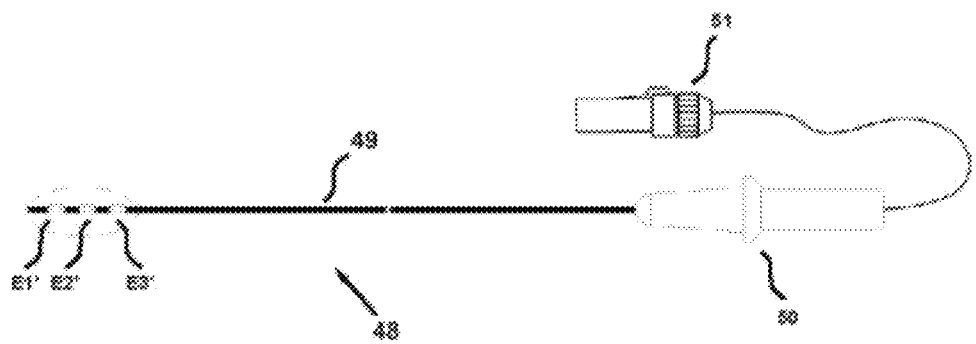
Figure 10C:
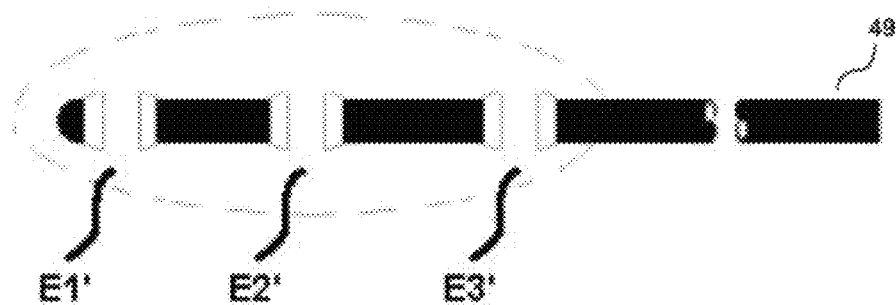

Referring now to FIGS. 10A-10C, shown therein is another example embodiment of a multi-polar electrode configuration for use with a multi-purpose catheter probe CP6. In this example a tripolar electrode configuration is shown however this design can be extended to probes that use one, two, three, four or more electrodes. The multi-purpose catheter probe is constructed from two sections. A first section 45, that forms part of a catheter probe (see FIG. 10A) has at its distal end three electrodes E1, E2, and E3 comprised of tightly wound coils of surgical grade stainless steel separated by insulated rings or insulated collars 46. Alternatively, the electrodes E1, E2, and E3 can be cylindrical stainless steel shells, or mesh, or other patterns and morphologies. The remaining proximal portion 47 of the first section 45 is comprised substantially of a coil, similar to the coil 10, that has a lumen, is tubular, is insulated on an outer portion thereof but provides an inner conductive pathway, and is flexible. A second section 48, shown in FIG. 10B, has spaced apart cylindrical conductive surfaces E1', E2', and E3' mounted on a distal portion of a flexible, insulated catheter probe 49, a handle (i.e. hub) 50, and a connector plug 51. The catheter probe 49 contains within its lumen insulated electrical leads that connect the cylindrical conductive surfaces E1', E2', and E3' to the connector plug 51 either directly or via intermediate electrical connections within the handle 50 and then terminate in the connector plug 51. Alternatively, thin wires can start at the conductive surfaces E1', E2' and E3' and pass though the catheter probe 49 and then inside the handle 50 to the intermediate electrical connections. Those wires could simply be soldered to other wires (for example thin wires will be soldered to thick, possibly multi-strand wires that will improve the mechanical strength of the wires). The thicker wires can then continue inside the cable and finally terminate at the connector plug 51. The lumen of the catheter probe 49 may also include other components such as thermocouple temperature sensors positioned at the cylindrical conductive surfaces E1', E2', and E3' or elsewhere such as within the lumen of the catheter probe 49 in close proximity to the conductive surfaces E1', E2', and E3'. Leads from these temperature sensors can also continue within the catheter probe 49 to the connector plug 51 either directly or via intermediate electrical connections within the handle 50. The end portion of the second section 48 that has the conductive surfaces E1', E2' and E3' has a smaller outer diameter than the inner diameter of the electrodes E1, E2 and E3 and the insulated rings 46 of the first section 45. This allows the electrodes E1, E2 and E3, the insulated rings 46 and the proximal portion 47 of the first section 45 to be slid over the distal portion of the second section 48 so that the electrodes E1, E2 and E3 are in electrical contact with the conductive surfaces E1', E2' and E3' with the insulated rings 46 in between the electrodes E1, E2 and E3.

FIG. 10C shows an enlarged view of the cylindrical conductive surfaces portion of the second section 48. The scale used in the enlarged view is the same as that for FIG. 10A in order to make it apparent that when the second section 48 is inserted within the first section 45, the cylindrical conductive surfaces E1', E2', and E3' will contact the interior of the electrodes E1, E2, and E3 respectively, thereby completing the electrical connection between the electrodes E1, E2, and E3 and the connector plug 51.

Portions or substantially all of the electrodes E1, E2, and/or E3 in this or other described embodiments can be more loosely wound to allow for the infusion of fluid into surrounding tissue or body spaces during use. To provide for the infusion of fluid, a similar design as that shown in FIG. 3 can be used. The fluid can be infused between the inner surface of the first section 45 and the outer surface of the second section 48. Slots or groves and the like can be used in the conductive surfaces E1', E2' and E3' to allow for the passage of fluid to and through the electrodes E1, E2, and E3. If the electrodes E1, E2, and E3 are configured as stainless steel cylindrical shells, or other morphologies that similarly have a continuous surface, exit holes, grids, slots, or other openings in these surfaces can be used as an outlet to allow for fluid infusion into the surrounding tissue during use. Such openings can be also be placed in one or more of the insulated sections separating the electrodes, or in other sections that are distal or proximal to the electrodes E1, E2, and E3, in addition to or instead of the openings or loose winding portions in the electrodes E1, E2, and E3. Alternatively, instead of openings in these surfaces, the proximal end of the first section 45 can be provided with an injection port/hub (not shown) to allow for the injection of fluid which traverses along the length of section 45 for exiting at its distal end; this occurs prior to the insertion of second section 48 into first section 45.

Figure 11:
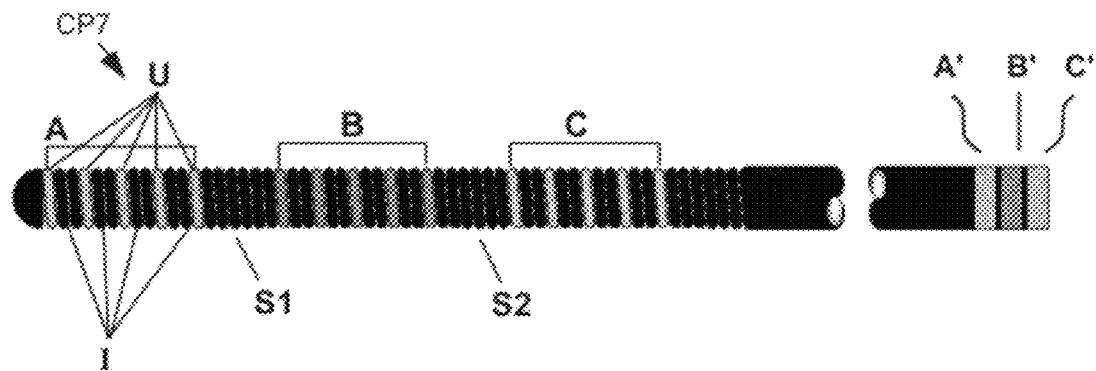
FIG. 11 shows a detailed view of another example embodiment of a tripolar multi-purpose catheter probe.

Referring now to FIG. 11, shown therein is a partial view of another example embodiment of a multi-polar electrode configuration for a multi-purpose catheter probe CP7. A tripolar electrode configuration is shown as an example, however, it should be understood that this design can be extended to a probe having one, two, three, four or more electrodes. The distal end of the multi-purpose catheter probe CP7 has three electrodes A, B, and C, and the proximal end has conductive surfaces A', B', and C' to allow for electrical connection in the hub (not shown) to the electrodes A, B and C. The electrodes A, B and C generally comprise alternating insulated and uninsulated sections. The electrodes A, B and C and the sections S1 and S2 separating the electrodes are of coil construction, with uninsulated coils drawn in a light color and insulated coils drawn in a dark color. This has also been identified for illustrative purposes for only electrode A in which the insulated coils are identified by the letter I and the uninsulated coils are identified by the letter U. In this example embodiment, each electrode A, B and C comprises alternating uninsulated and insulated coils in which there are five uninsulated coils, with each uninsulated coil being separated by two insulated coils. However, in alternative embodiments, there can be more or fewer uninsulated coils, the number of which can be selected depending on the particular application of the multi-purpose catheter probe CP7. In some embodiments, each electrode A, B and C has more insulated than uninsulated coils. In general, there can be various combinations of insulated and uninsulated coils at various ratios such as 1:1, 1:3, 2:3 and the like where the first number represents uninsulated coils and the second number represents insulated coils.

This design technique can be referred to as spread impedance or linear disposition of the electrodes since each electrode A, B and C have a smaller surface area that is in contact or close proximity with the surrounding tissue. This is in contrast to an electrode that is completely uninsulated which therefore has a larger conductive surface area which results in greater conductivity of electricity, a lower electrode impedance and a higher current during lesion. Therefore, the electrodes A, B and C may have the same length as electrodes that are completely uninsulated, however the electrodes A, B and C have a smaller conductivity and higher impedance since portions of the electrodes A, B and C are insulated. The benefit of the increased resistance R at each electrode A, B and C and tissue or fluid interface, is that any desired level of heat can be generated, which is proportional to $I^2 \times R$, where I is lesion current, with smaller levels of current or in other words lower current density. Current density on the surface of an electrode will lead to carbonization of the tissue if the current density is too high. Furthermore, the distributed conductive coils in each electrode A, B and C can transfer heat to the insulated portions of these electrodes A, B and C to help sink heat that is generated during lesioning. This maintains the electrodes A, B and C at a lower temperature without the need of a cooling fluid mechanism and also helps to reduce carbonization of the tissue that surrounds these electrodes A, B and C. Accordingly, in use, the electrodes A, B and C prevent tissue from heating up too rapidly and also prevent tissue charring on their surfaces. Furthermore, having a lower current and impedance spread along the shaft of the catheter probe results in a more uniform and larger lesion with less carbonization of the tissue.

It should also be noted that the linear disposition of the electrodes A, B and C with insulated and uninsulated portions, as shown in FIG. 11, can be used to generate long, linear lesions as required by some therapeutic applications without requiring the use of electrode-cooling liquids to prevent electrode overheating as is associated with more conventional electrode constructions. Accordingly, as used herein, the term "linearly disposed electrode" means that the conductive portions of a single electrode are interspersed with insulative portions along the longitudinal axis of the coil electrode as shown by the example in FIG. 11.

Figures 12A, 12B:
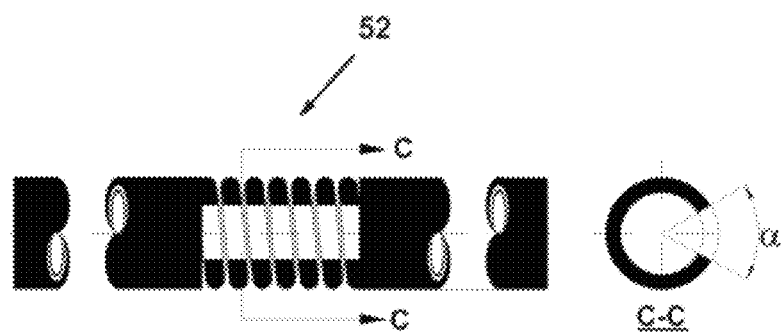
FIG. 12A shows a modification of the electrode section(s) that can be made to any of the multi-purpose catheter probes described herein in which the electrode surface is partially insulated to confer directional control of ablation current.
FIG. 12B shows sectional views through an electrode section of FIG. 12A.

Although no polymer coating is used in the electrode sections of the stainless steel coils or conductive cylinders in the monopolar, bipolar, and tripolar embodiments of the multi-purpose catheter probes described above, such coating could be beneficially used over a portion of the circumference of the coils, cylinders, or other electrode configurations. For example, as shown in FIG. 12B, which is a cross-sectional view along the longitudinal axis of an electrode coil 52 taken at section C-C of FIG. 12A, a polymer insulation has been applied to circumferentially cover the electrode 52 over all but an uninsulated portion defined by an arc of α degrees, which can be 60° for example. The intended effect of this partial circumferential insulation is to limit the exit of ablation current to the uninsulated longitudinal strip of the electrode coil 52 (this can be done for at least one, and in some cases, all electrodes in a multi-polar catheter probe). In this manner ablation current could be directed toward or away from certain tissue regions, such as, for example, toward tissue that is an ablation target, or away from tissue that is to be protected. The orientation and location of the uninsulated longitudinal strip could be determined, for example, fluoroscopically by a radiopaque marker in the proximity of the electrode coil 52, by a radiopaque ring strategically located along the tubular catheter body, and/or by another marker on an external portion of the multi-purpose catheter probe such as its proximal hub.

Figure 13A:
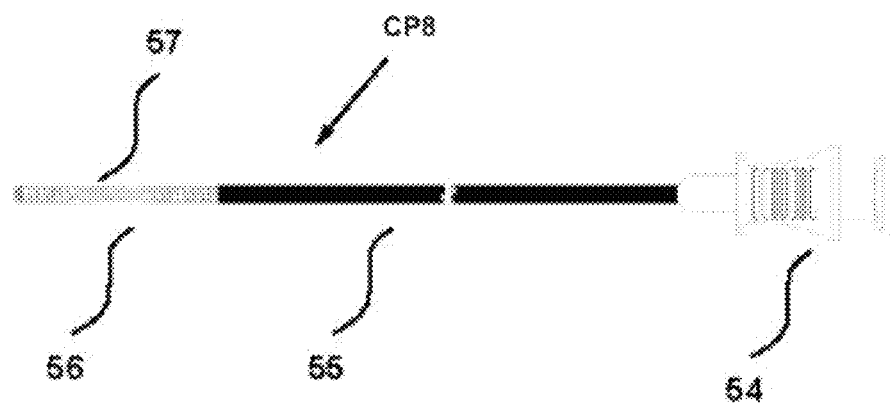
FIGS. 13A-D show detailed views of another example embodiment of a multi-purpose catheter probe that can be used beneficially with other commercially available products such as spinal catheters and spinal endoscopes.
Figure 13B:
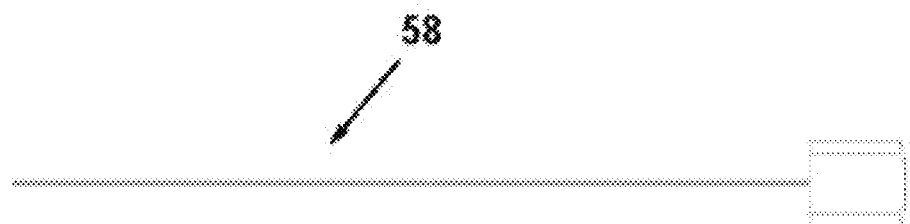

Referring now to FIGS. 13A-D, shown therein is another example embodiment of a multi-purpose catheter probe CP8 with a design that allows it to be used with other commercially available products such as spinal catheters and spinal endoscopes. The design of the multi-purpose catheter probe CP8 can be applied to the other embodiments described herein. FIG. 13A shows, for example, that the multi-purpose catheter probe CP8 is similar to the multi-purpose catheter probe CP1 of FIG. 1, since it comprises a proximal hub 54, a tubular catheter body 55, and a catheter distal end 56. The tubular catheter body 55 and the catheter distal end 56 can be constructed from a tightly wound continuous coil 57 of surgical grade stainless steel that has a smooth polymer coating over the tubular catheter body 55 but not over the catheter distal end 56 which is uninsulated so that the catheter distal end can act as an electrode when desired. The length of the tubular catheter body 55 is typically about 25 to 30 cm, but for certain applications it can be as short as 10 cm or less, or as long as 60 cm or more, and its outer diameter is typically about 18 gauge (1.27 mm) to 20 gauge (0.91 mm). The length of the catheter distal end 56 is typically about 5 mm to 15 mm, although it can be 10 mm in some cases, and in general can be in the range of about 2 mm to 25 mm. Variations in length, diameter and gauge can clearly be used according to the desired application and are not limited to the ranges given herein.

Figure 13C:
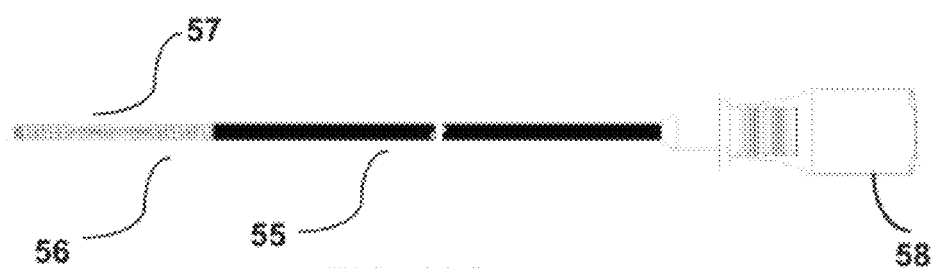
Figure 13D:
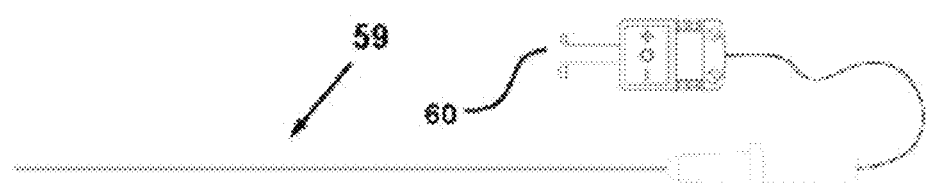

The multi-purpose catheter probe CP8 has associated with it separate members comprising a stylet 58 (see FIG. 13B), a thermocouple probe 59 (see FIG. 13D) and a connector plug 60. FIG. 13C shows the stylet 58 in place within the multi-purpose catheter probe CP8 as may be required during a percutaneous approach of the multi-purpose catheter probe CP8 to a target region. The stylet 58 can provide the required stiffness and preferential bending for the catheter probe CP8. The thermocouple probe 59 can be considered to be similar to the earlier embodiments in which the tube 11 was used as part of a thermocouple probe. The thermocouple probe 59 can also be used to conduct electrical signals from the connector plug 60 to the electrode in the catheter distal end 57.

From the above it can be appreciated that unlike the previously described multi-purpose catheter probe embodiments, the multi-purpose catheter probe CP8 does not have as integral members a special fluid injection port through which medications and other fluids can be directed into tissue or fluid spaces, nor a thermocouple probe for monitoring tissue temperature. However, both of these functions are available to the multi-purpose catheter probe CP8. Fluid injection into the multi-purpose catheter probe CP8 is possible via the proximal hub 54, which is shown here as a commonly used luer type connector with a channel for accepting a fluid-filled syringe, an IV delivery system, the stylet 58, the thermocouple catheter probe 59 or the output of a pump. The fluid-filled syringe and IV delivery system are just a few examples of the various devices that can be attached to the hub 54 for fluid injection or extraction. The hub 54 can be permanently attached to the catheter body 55 or it can be detachable in which case the catheter body 55 can be left implanted within a patient if desired. The tissue temperature can be monitored during the lesion process by inserting a thermocouple probe 59 (see FIG. 13D) within the multi-purpose catheter probe CP8 via the channel of the proximal hub 54. The thermocouple probe 59 is then connected to a temperature sensing module via the connector plug 60. Electrical stimulation, electrical impedance measurement, and RF ablation are implemented at the catheter distal end 56 of the multi-purpose catheter probe CP8 in the manner described for the multi-purpose catheter probe CP1 of FIG. 1. Furthermore, the catheter probe CP8 can be disassembled and the catheter body 55 can be left implanted in a patient if desired.

As is the case for the previously described multi-purpose catheter probes, the stainless steel coil 57 is tightly wound along its entire length except over a portion of the catheter distal end 56 where it is more loosely wound, here shown in its middle section, to allow for the infusion of injected fluid into surrounding tissue or body spaces during use. Furthermore, the coil 57 extends along a substantial and in some cases the entire, portion of the catheter body 55 to provide flexibility.

It should be noted that it is possible to implement at least some of the various embodiments herein using rigid or flexible plastic tubing (which may be obtained from an extruded plastic process for example) in which at least one electrode can be created on a single catheter probe by placing at least one ring along the length of the catheter probe body by etching away the plastic exterior of the catheter probe body. The technique of creating directional lesioning as well as spread impedance/current can also be attained by using a rigid or flexible plastic tubing and etching away some of the insulation on the rings to obtain a special pattern.

It should also be noted that for at least some cases of the multi-purpose catheter probes described herein, it is possible to place a temperature sensor near every electrode, which will allow for full control of the lesion that is being created in use since the temperature can be monitored at each electrode. Furthermore, the multi-polar embodiments of the catheter probe described herein allow for greater control of the lesion that is created in use due to the ability to control each electrode independently of one another. For example, the multi-polar embodiments of the catheter probe described herein can be used to create irregularly shaped lesions to treat irregularly shaped tumors or irregularly shaped tissue regions.

It should also be noted that there can be other embodiments of the catheter probes described herein in which the electrodes have different lengths, and/or different outer diameters and/or are distributed unevenly along the length of the catheter probe. Such embodiments may provide additional benefits depending on the particular application.

It should also be noted that other catheter probes have an electrode ring or the like placed on a plastic shaft of the catheter probe. This design restricts thermal exchange between the electrode ring and the shaft due to the limited thermal conductivity of plastic. This is particularly a disadvantage during high power lesioning as the surface of the electrode is heated due to the current flowing from the electrode to the tissue. In these cases, cooling of the electrode is needed in order to avoid carbonization of the tissue on the surface of the rings. However, the design of the various embodiments of the multi-purpose catheter probes described herein allows for most heat that is generated during lesioning to be dispersed along a portion of the catheter body since the catheter body is formed by a coil which is made from some type of metal and therefore acts as a much better heat sink than plastic. This allows for the surface of the electrode(s) of the various catheter probes described herein to remain at lower temperatures, which would allow for the delivery of more RF current to achieve larger lesions without carbonization of the surrounding tissue.

It should be noted that catheter probes can be designed that utilize some of the structural features described herein while not providing all of the various functions described herein, but rather a subset of the functions described herein. For example, a catheter probe can be designed that uses a coil for a substantial portion of its body to provide enhanced flexibility. For example, it is also possible to construct the multi-polar catheter probes using some of the techniques described herein without adding temperature sensors or fluid delivery capabilities. Furthermore, for example, it is also possible to incorporate the thermocouple probe design described herein with various structural designs described herein to provide multi-polar electrodes without incorporating fluid delivery functionality.

It should also be noted that, in at least some of the embodiments described herein, the main coil 10 forms the catheter body and in some cases the distal end of the catheter probe. The main coil 10 serves to impart overall flexibility to the catheter probes and also provides a housing for the internal components of the catheter probes. In at least some of the embodiments described herein, the main coil 10 can provide a lumen to deliver fluid to the tip of the catheter probe, can act as an electrical conductor, and can act as a conduit for thermocouple sensors and/or electrical wires that can be placed within it.

It should also be understood that other elements can be used instead of the coil 10, which provide the same benefits as the coil 10. This substitution not only applies for the catheter probes CP1 and CP2 but can also be done with the various other embodiments of the catheter probes that are described herein. Furthermore, this substitution can be made for the other coils that extend along a substantial part of the catheter probe such as the first member 21 and the second member 23 in the catheter probe CP3, the third member 34 in the catheter probe CP4, a portion of the catheter probe section 41 of the catheter probe CP5, a portion of the second section 48 of the catheter probe CP6, a proximal section of the catheter probe CP7 and a portion of the tubular catheter body 55 of the catheter probe CP8. In each of these cases, the coil 10 and the other elements just mentioned that perform similar functions, can be replaced with a flexible tube that is conductive. The tube can be made from fine gauge Nitinol, stainless steel (such as 30 Gauge for example) and the like. The coil 10 and the corresponding elements listed above in the other embodiments of the catheter probes can be referred to as a channel member. Generally, the channel member has an inner conductive surface, a conduit for carrying electrical wires and is flexible to provide enhance the maneuverability of the catheter probe while providing the strength that is required for mechanical stability. The channel member is fairly continuous to allow for the passage of fluid. Accordingly, if the channel member is made from a coil, the coil is tightly wound although there could be embodiments in which the channel member is made from an element that is not continuous and an additional layer is added to the outside of the channel member to allow the channel member to carry fluids.

While the applicant's teachings described herein are in conjunction with various embodiments for illustrative purposes, it is not intended that the applicant's teachings be limited to such embodiments or to the described regions of the body. On the contrary, the applicant's teachings encompass various alternatives, modifications, and equivalents, and can find diagnostic and therapeutic use in other regions such as muscle, skin, brain, lung, liver, breast, kidney and prostate tissue as will be appreciated by those skilled in the art.

The invention claimed is:

1. A catheter probe comprising:
    a proximal hub comprising a hub housing, a single lead wire and a third wire;
    a catheter body connected to the proximal hub, the catheter body comprising:
        a channel member being adapted to provide a housing for a portion of the catheter body, the channel member being conductive to provide a conductive pathway, and the channel member comprising a lumen;
        an insulator being disposed so at least a portion of the channel member is uninsulated; and
        a tube located within the lumen of the channel member and housing the single lead wire, the tube having a proximal end and a distal end, the tube and the single lead wire extending from the hub to the catheter distal end, the single lead wire having a first end that extends externally of the hub to electrically connect with an external temperature monitoring module and a second end that is electrically connected to the distal end of the tube to form a first hot thermocouple junction and being insulated between the first and second ends, and the third wire is electrically connected between the proximal end of the tube and the external temperature monitoring module to form a cold thermocouple junction at the external temperature monitoring module to provide a first thermocouple for the catheter probe, wherein the tube is conductive and provides a conductive return path from a point of attachment of the first hot thermocouple junction to the third wire; and
    a catheter distal end comprising at least one electrode electrically connected to the tube.

2. The catheter probe of claim 1, wherein the channel member is adapted to provide the housing for a substantial portion of the catheter body.

3. The catheter probe of claim 1, wherein the catheter distal end comprises several electrodes that are spaced apart from one another and have a common diameter.

4. The catheter probe of claim 1, wherein the at least one electrode comprises a coil that is loosely wound to allow a fluid to be ejected from the catheter probe in use.

5. The catheter probe of claim 1, wherein the channel member extends into the catheter distal end and the at least one electrode comprises an uninsulated portion of the channel member in the catheter distal end.

6. The catheter probe of claim 1, wherein the at least one electrode can be used to provide at least one of an electrical stimulus, RF ablation energy and an impedance measurement contact.

7. The catheter probe of claim 1, wherein the catheter probe further comprises:
    a fluid injection port to receive a fluid in use; and
    a plastic tubing that extends from the fluid injection port into the hub, the plastic tubing having a first opening for receiving the fluid from the fluid injection port and a second opening extending between an inner wall of the channel member and an outer surface of the tube,
    wherein, in use, the fluid is provided from the plastic tubing through the second opening to the catheter body.

8. The catheter probe of claim 1, wherein the catheter probe further comprises:
    a fourth wire at the proximal hub;
    a cylindrical insulator having a proximal portion and a distal elongated portion having a smaller outer diameter than the proximal portion; and an end portion formed by a distal end of the tube; and
wherein the at least one electrode comprises:
  a first coil electrode that is on the elongated portion of the cylindrical insulator and is electrically coupled to the tube; and
  a second coil electrode that is formed by a distal portion of the channel member that is uninsulated and is coupled to the fourth wire,
wherein the cylindrical insulator is on the tube and is located adjacent the second coil electrode and the first coil electrode is located between the proximal portion of the cylindrical insulator and the end portion of the tube.

9. The catheter probe of claim 8, wherein the catheter probe comprises a second lead wire at the proximal hub, the second lead wire having a first end that extends externally of the hub to electrically connect with the external temperature monitoring module and a second end that is electrically connected to a portion of the tube near the second coil electrode to form a second hot thermocouple junction for a second thermocouple and being insulated between the first and second ends, wherein the tube is conductive and provides an electrical connection from a second point of attachment of the second hot thermocouple junction to the third wire, and the third wire is electrically connected between the proximal end of the tube and the external temperature monitoring module to form the cold thermocouple junction to provide a second thermocouple for the catheter probe to allow the catheter probe to be used as a thermocouple probe having two thermocouples, wherein the tube is conductive and provides a conductive return path for the cold thermocouple junction starting from the first and second points of attachment of the first and second hot thermocouple junctions respectively to the third wire.

10. The catheter probe of claim 1, wherein the at least one electrode comprises first and second coil electrodes the catheter probe comprises:
  an insulated collar; and
  a first member defining the catheter distal end, the first member comprising the first coil electrode having an uninsulated coil portion at a distal portion thereof and an insulated coil portion proximal to the first coil electrode to provide an electrical connection between the first coil electrode and an electrical connector within the hub, the first coil electrode having a diameter larger than the proximal coil portion; and
  a distal portion of the channel member is uninsulated to provide the second coil electrode and the channel member comprises a lumen having a diameter larger than the diameter of the insulated coil portion of the first member,
wherein the insulated collar is located between the first and second coil electrodes, and the insulated coil portion of the first member is located within the lumen of the channel member.

11. The catheter probe of claim 1, wherein the at least one electrode comprises first and second coil electrodes and the catheter probe comprises:
  an insulated collar;
  a first member defining the catheter distal end, the first member comprising the first coil electrode that is uninsulated at a distal portion thereof and an insulated wire portion proximal to the first coil electrode to provide an electrical connection between the first coil electrode and a first electrical connector within the hub; and
  a distal portion of the channel member is uninsulated to provide the second coil electrode, the channel member comprises a lumen and the channel member is connected to a second electrical connector within the hub,
wherein the insulated collar is located between the first and second coil electrodes, and the wire portion of the first member is located within the lumen of the channel member.

12. The catheter probe of claim 11, wherein the first coil electrode has a proximal portion with a smaller diameter than the uninsulated portion of the first coil electrode, the second coil electrode has a distal portion with a smaller diameter than the uninsulated portion of the second coil electrode and the insulated collar has an inner diameter such that inner portions of the insulated collar contact the smaller diameter portions of the first and second coil electrodes.

13. The catheter probe of claim 12, wherein the smaller diameter portions of the first and second coil electrodes are insulated.

14. The catheter probe of claim 1, wherein the at least one electrode comprises first, second and third coil electrodes and the catheter probe comprises:
  first and second insulated members;
  a first member defining the catheter distal end, the first member comprising the first coil electrode that is uninsulated at a distal portion thereof and a first insulated wire portion proximal to the first coil electrode to provide an electrical connection between the first coil electrode and a first electrical connector within the hub;
  a second member also defining the catheter distal end, the second member comprising the second coil electrode that is uninsulated at a distal portion thereof and a second insulated tubular wire portion proximal to the second coil electrode to provide an electrical connection between the second coil electrode and a second electrical connector within the hub; and
  a distal portion of the channel member is uninsulated to provide the third coil electrode, the channel member comprises a lumen and the channel member is connected to a third electrical connector within the hub,
wherein the first insulated member is located between the first and second coil electrodes, the second insulated member is located between the second and third coil electrodes, and the first and second wire portions are located within the lumen of the channel member.

15. The catheter probe of claim 1, wherein the hub is releasably attachable with a proximal portion of the catheter body, the proximal portion of the catheter body comprises at least one electrical contact and the hub comprises a corresponding at least one electrical contact that is adapted to electrically connect with the at least one electrical contact of the proximal portion of the catheter body when the hub is attached to the catheter body.

16. The catheter probe of claim 15, wherein the hub comprises a channel and the catheter body comprises a lumen defined by the channel member, the hub is adapted to releasably receive a stylet having a shaft and the channel and the lumen are sized to receive the shaft of the stylet.

17. The catheter probe of claim 1, wherein:
  the channel member comprises at least two conductive surfaces spaced apart from one another on a distal portion of the channel member, a lumen and at least two electrical leads within the lumen that connect to the at least two conductive surfaces,
  the hub comprises at least two intermediate electrical connections that are connected to the at least two electrical leads; and
  the catheter distal end comprises at least two electrodes and an insulator ring positioned there between, the at least two electrodes being adapted to electrically engage the at least two conductive surfaces.

18. The catheter probe of claim 1, wherein the at least one electrode comprises several sets of alternating insulated and uninsulated sections.

19. The catheter probe of claim 18, wherein the at least one electrode comprises a coil electrode comprising several sets of alternating uninsulated and insulated coils.

20. The catheter probe of claim 19, wherein the coil electrode comprises more insulated coils than uninsulated coils.

21. The catheter probe of claim 1, wherein the channel member is adapted to provide a housing for the catheter distal end and a portion of the channel member is uninsulated to provide the at least one electrode, and wherein the hub comprises a channel to receive one of a stylet and a thermocouple catheter probe in use.

22. Use of a catheter probe as defined in claim 1 for therapeutic treatment of a target tissue region, wherein the use comprises:
  placing the distal catheter end in close proximity to the target tissue region;
  applying a radiofrequency current to the at least one electrode to ablate a portion of the target tissue region; and
  measuring an impedance using the at least one electrode to determine effectiveness of the treatment.

23. The use as claimed in claim 22, wherein the use further comprises applying a stimulus current to the at least one electrode prior to applying the radiofrequency current to determine that the catheter probe is correctly located.

24. The use as claimed in claim 22, wherein the catheter probe is further defined as in claim 7 and the use further comprises monitoring a temperature of the target tissue region for at least one of before, during and after delivery of the radiofrequency current.

25. The use as claimed in claim 22, wherein the catheter probe is further defined as in claim 8 and the use further comprises delivering a fluid to the target tissue region.

26. A catheter probe comprising:
  a proximal hub comprising a hub housing and first and second lead wires, a third wire and a fourth wire;
  a catheter body connected to the proximal hub, the catheter body comprising:
    a channel member being adapted to provide a housing for a portion of the catheter body, the channel member being conductive to provide a conductive pathway and being electrically coupled to the proximal hub by the fourth wire, and the channel member comprising a lumen;
    an insulator being adapted to cover at least a portion of the channel member;
    a tube located within the lumen of the channel member and housing the first and second lead wires, the tube having a proximal end and a distal end, the tube and the first and second lead wires extending from the hub to the catheter distal end, the first lead wire having a first end that extends externally of the hub to electrically connect with an external temperature monitoring module and a second end that is electrically connected to the distal end of the tube to form a first hot thermocouple junction for a first thermocouple and being insulated between the first and second ends, the second lead wire having a first end that extends externally of the hub to electrically connect with the external temperature monitoring module and a second end that is electrically connected to a portion of the tube near a second coil electrode to form a second hot thermocouple junction for a second thermocouple and being insulated between the first and second ends, and the third wire is electrically connected between the proximal end of the tube and the external temperature monitoring module to form a cold thermocouple junction for the first and second thermocouples at the external temperature monitoring module to allow the catheter probe to be used as a thermocouple probe having two thermocouples, wherein the tube is conductive and provides a conductive return path from the first and second hot thermocouple junctions to the third wire; and;
    a cylindrical insulator having a proximal portion and a distal elongated portion having a smaller outer diameter than the proximal portion;
    a first coil electrode that is on the elongated portion of the cylindrical insulator that is electrically connected to the tube;
    an end portion formed by a distal end of the tube; and
    a distal portion of the channel member is uninsulated to provide the second coil electrode,
  wherein the cylindrical insulator is on the tube and is located adjacent the second coil electrode and the first coil electrode is located between the proximal portion of the cylindrical insulator and the end portion of the tube.

27. A catheter probe comprising:
  a proximal hub comprising a hub housing and electrical connectors;
  a catheter body connected to the proximal hub, the catheter body comprising:
    a first member defining a catheter distal end, the first member comprising an uninsulated first coil electrode at a distal portion thereof and a proximal coil portion that is conductive and has an outer insulated layer and is proximal to the first coil electrode to provide an electrical connection between the first coil electrode and an electrical connector within the proximal hub, the first coil electrode having a diameter larger than the proximal coil portion;
    a channel member being adapted to provide a housing for a portion of the catheter body, the channel member being conductive to provide a conductive pathway, and a distal portion of the channel member is uninsulated to provide a second coil electrode and the channel member comprises a lumen having a diameter larger than the diameter of the insulated coil portion of the first member, the channel member being electrically connected to a second electrical connector within the proximal hub,
    an insulator being adapted to cover at least a portion of the channel member; and
    an insulated collar located between the first and second coil electrodes,
  wherein the insulated coil portion of the first member is located within the lumen of the channel member.

28. A catheter probe comprising:
  a proximal hub comprising a hub housing and electrical connectors;
  a catheter body connected to the proximal hub, the catheter body comprising:
    a first member defining a catheter distal end, the first member comprising an uninsulated first coil electrode at a distal portion thereof and an conductive wire portion with an insulated outer layer proximal to the first coil electrode to provide an electrical connection between the first coil electrode and a first electrical connector within the hub;
    a channel member being adapted to provide a housing for a portion of the catheter body, the channel member being conductive to provide a conductive pathway, a distal portion of the channel member being uninsulated to provide a second coil electrode, the channel member comprising a lumen and being connected to a second electrical connector within the hub;

an insulator being adapted to cover at least a portion of the channel member; and an insulated collar being located between the first and second coil electrodes, and wherein the wire portion of the first member is located within the lumen of the channel member.

29. A catheter probe comprising:

a proximal hub comprising a hub housing and electrical connectors;

a catheter body connected to the proximal hub, the catheter body comprising:

first and second insulated members;

a first member defining a catheter distal end, the first member comprising an uninsulated first coil electrode at a distal portion thereof and a first conductive wire portion with an insulated layer proximal to the first coil electrode to provide an electrical connection between the first coil electrode and a first electrical connector within the hub;

a second member also defining the catheter distal end, the second member comprising an uninsulated second coil electrode at a distal portion thereof and a second conductive tubular wire portion with an insulated layer proximal to the second coil electrode to provide an electrical connection between the second coil electrode and a second electrical connector within the hub;

a channel member being adapted to provide a housing for a portion of the catheter body, the channel member being conductive to provide a conductive pathway and a distal portion of the channel member being uninsulated to provide a third coil electrode, the channel member comprising a lumen and the channel member being connected to a third electrical connector within the hub, and an insulator being adapted to cover at least a portion of the channel member, wherein the first insulated member is located between the first and second coil electrodes, the second insulated member is located between the second and third coil electrodes, and the first and second wire portions are located within the lumen of the channel member.

* * * * *